United States Patent
Sequin et al.

(10) Patent No.: US 8,236,041 B2
(45) Date of Patent: *Aug. 7, 2012

(54) NONCYLINDRICAL STENT DEPLOYMENT SYSTEM FOR TREATING VASCULAR BIFURCATIONS

(75) Inventors: Jacques Sequin, Old Windsor (GB); Robert John Elicker, Santa Margarita, CA (US); Jean-Claude Laborde, Vielle-Toulouse (FR)

(73) Assignee: Biosensors International Group, Ltd., Hamilton (BM)

(*) Notice: Subject to any disclaimer, the term of this patent is extended or adjusted under 35 U.S.C. 154(b) by 608 days.

This patent is subject to a terminal disclaimer.

(21) Appl. No.: 10/976,564

(22) Filed: Oct. 29, 2004

(65) Prior Publication Data

US 2005/0096726 A1   May 5, 2005

Related U.S. Application Data

(60) Division of application No. 10/282,957, filed on Oct. 28, 2002, now Pat. No. 7,125,419, which is a continuation of application No. 10/225,484, filed on Aug. 20, 2002, now Pat. No. 7,238,197, which is a continuation-in-part of application No. 09/580,597, filed on May 30, 2000, now Pat. No. 6,666,883.

(51) Int. Cl.
 *A61F 2/06*   (2006.01)
(52) U.S. Cl. ..................................... 623/1.12
(58) Field of Classification Search ........ 623/1.11–1.54; 128/898
See application file for complete search history.

(56) References Cited

U.S. PATENT DOCUMENTS

| | | |
|---|---|---|
| 3,657,744 A | 4/1972 | Ersek |
| 3,805,301 A | 4/1974 | Liebig |
| 3,818,511 A | 6/1974 | Goldberg et al. |
| 3,945,052 A | 3/1976 | Liebig |
| 4,390,599 A | 6/1983 | Broyles |
| 4,562,596 A | 1/1986 | Kornberg |
| 4,733,065 A | 3/1988 | Hoshi et al. |

(Continued)

FOREIGN PATENT DOCUMENTS

EP   0335 341 B1   3/1992

(Continued)

OTHER PUBLICATIONS

Abizaid et al., One-Year Follow-up After Intravascular Ultrasound Assessment of Moderate Left Main Coronary Artery Disease in Patients with Ambiguous Angiograms, JACC vol. 34, No. 3 1999, pp. 707-715; © 1999 by the American College of Cardiology; Published by Elsevier Science, Inc.

(Continued)

*Primary Examiner* — Katherine Dowe
(74) *Attorney, Agent, or Firm* — Kilpatrick Townsend & Stockton LLP

(57) ABSTRACT

A device and method for treating pathological narrowing of fluid-carrying conduits of the human body (such as blood vessels) in an area of a bifurcation is disclosed. In particular, a stent system carries a self expandable noncylindrical stent, which is particularly suited for treating a widened portion of a blood vessel immediately proximal to a bifurcation. A stent delivery system is also disclosed, for delivering the stent such that a larger expanded diameter end of the stent faces the bifurcation, and a smaller expanded diameter end of the stent faces proximally in the main vessel.

19 Claims, 14 Drawing Sheets

U.S. PATENT DOCUMENTS

| | | | |
|---|---|---|---|
| 4,733,665 A | 3/1988 | Palmaz | |
| 4,768,507 A | 9/1988 | Fischell et al. | |
| 4,800,882 A | 1/1989 | Gianturco | |
| 4,806,062 A | 2/1989 | Stier | |
| 4,886,062 A | 12/1989 | Wiktor | |
| 4,994,071 A | 2/1991 | MacGregor | |
| 5,019,090 A | 5/1991 | Pinchuk et al. | |
| 5,045,072 A | 9/1991 | Castillo et al. | |
| 5,064,435 A | 11/1991 | Porter | |
| 5,102,417 A | 4/1992 | Palmaz | |
| 5,104,404 A | 4/1992 | Wolff | |
| 5,135,536 A | 8/1992 | Hillstead | |
| 5,192,297 A | 3/1993 | Hull | |
| 5,195,984 A | 3/1993 | Schatz | |
| 5,197,978 A | 3/1993 | Hess | |
| 5,211,658 A | 5/1993 | Clouse et al. | |
| 5,211,663 A | 5/1993 | Kovacs et al. | |
| 5,219,355 A | 6/1993 | Parodi et al. | |
| 5,234,457 A * | 8/1993 | Andersen | 606/198 |
| 5,282,824 A | 2/1994 | Gianturco | |
| 5,330,500 A | 7/1994 | Song | |
| 5,356,423 A | 10/1994 | Tihon et al. | |
| 5,360,401 A | 11/1994 | Turnland | |
| 5,360,443 A | 11/1994 | Barone et al. | |
| 5,370,683 A | 12/1994 | Fontaine | |
| 5,387,235 A | 2/1995 | Chuter | |
| 5,443,498 A | 8/1995 | Fontaine | |
| 5,445,646 A | 8/1995 | Euteneuer et al. | |
| 5,456,713 A | 10/1995 | Chuter | |
| 5,466,242 A | 11/1995 | Mori | |
| 5,499,973 A | 3/1996 | Saab | |
| 5,514,154 A | 5/1996 | Lau et al. | |
| 5,514,178 A | 5/1996 | Torchio | |
| 5,540,701 A | 7/1996 | Sharkey et al. | |
| 5,562,697 A | 10/1996 | Christiansen | |
| 5,562,724 A | 10/1996 | Vorwerk et al. | |
| 5,562,726 A | 10/1996 | Chuter | |
| 5,571,135 A | 11/1996 | Fraser | |
| 5,571,168 A | 11/1996 | Toro | |
| 5,571,170 A | 11/1996 | Palmaz et al. | |
| 5,571,173 A | 11/1996 | Parodi | |
| 5,591,228 A * | 1/1997 | Edoga | 128/898 |
| 5,603,721 A | 2/1997 | Lau et al. | |
| 5,609,605 A | 3/1997 | Marshall et al. | |
| 5,609,627 A | 3/1997 | Goicoechea et al. | |
| 5,617,878 A | 4/1997 | Taheri | |
| 5,628,788 A | 5/1997 | Pinchuk | |
| 5,632,762 A | 5/1997 | Myler | |
| 5,632,763 A | 5/1997 | Glastra | |
| 5,632,771 A | 5/1997 | Boatman et al. | |
| 5,632,772 A | 5/1997 | Alcime et al. | |
| 5,639,278 A | 6/1997 | Dereume et al. | |
| 5,667,486 A | 9/1997 | Mikulich et al. | |
| 5,669,880 A | 9/1997 | Solar | |
| 5,669,924 A | 9/1997 | Shaknovich | |
| 5,676,696 A * | 10/1997 | Marcade | 623/1.35 |
| 5,683,449 A | 11/1997 | Marcade | |
| 5,683,451 A | 11/1997 | Lenker | |
| 5,693,084 A | 12/1997 | Chuter | |
| 5,695,499 A * | 12/1997 | Helgerson et al. | 606/108 |
| 5,707,376 A | 1/1998 | Kavteladze et al. | |
| 5,716,393 A | 2/1998 | Lindenberg et al. | |
| 5,720,735 A | 2/1998 | Dorros | |
| 5,720,776 A | 2/1998 | Chuter et al. | |
| 5,735,893 A | 4/1998 | Lau et al. | |
| 5,741,327 A | 4/1998 | Frantzen | |
| 5,749,825 A | 5/1998 | Fischell et al. | |
| 5,749,890 A | 5/1998 | Shaknovich | |
| 5,755,769 A | 5/1998 | Richard et al. | |
| 5,755,771 A | 5/1998 | Penn et al. | |
| 5,776,142 A | 7/1998 | Gunderson | |
| 5,776,184 A | 7/1998 | Tuch | |
| 5,788,707 A | 8/1998 | Del Toro et al. | |
| 5,797,951 A | 8/1998 | Mueller | |
| 5,797,952 A | 8/1998 | Klein | |
| 5,800,514 A | 9/1998 | Nunez et al. | |
| 5,800,520 A | 9/1998 | Fogarty et al. | |
| 5,820,542 A | 10/1998 | Dobak, III et al. | |
| 5,824,040 A | 10/1998 | Cox et al. | |
| 5,824,042 A | 10/1998 | Lombardi et al. | |
| 5,824,071 A | 10/1998 | Nelson et al. | |
| 5,827,321 A | 10/1998 | Roubin et al. | |
| 5,833,694 A | 11/1998 | Poncet | |
| 5,849,037 A | 12/1998 | Frid | |
| 5,851,217 A | 12/1998 | Wolff et al. | |
| 5,851,228 A | 12/1998 | Pinheiro | |
| 5,851,231 A | 12/1998 | Wolff et al. | |
| 5,873,904 A | 2/1999 | Ragheb et al. | |
| 5,891,114 A | 4/1999 | Chien et al. | |
| 5,893,887 A | 4/1999 | Jayaraman | |
| 5,897,588 A | 4/1999 | Hull et al. | |
| 5,904,713 A | 5/1999 | Leschinsky | |
| 5,910,129 A * | 6/1999 | Koblish et al. | 604/95.03 |
| 5,922,019 A | 7/1999 | Hankh et al. | |
| 5,938,697 A | 8/1999 | Killion et al. | |
| 5,957,930 A * | 9/1999 | Vrba | 623/1.11 |
| 5,957,949 A | 9/1999 | Leonhardt | |
| 5,961,548 A | 10/1999 | Shmulewitz | |
| 5,976,155 A | 11/1999 | Foreman et al. | |
| 5,980,484 A | 11/1999 | Ressemann et al. | |
| 5,980,533 A | 11/1999 | Holman | |
| 5,984,955 A | 11/1999 | Wisselink | |
| 5,989,280 A | 11/1999 | Euteneuer et al. | |
| 5,993,481 A | 11/1999 | Marcade et al. | |
| 6,010,530 A | 1/2000 | Goicoechea | |
| 6,030,415 A | 2/2000 | Chuter | |
| 6,042,588 A | 3/2000 | Munsinger et al. | |
| 6,042,606 A | 3/2000 | Frantzen | |
| 6,053,941 A | 4/2000 | Lindenberg et al. | |
| 6,056,776 A | 5/2000 | Lau et al. | |
| 6,059,813 A | 5/2000 | Vrba et al. | |
| 6,063,113 A | 5/2000 | Kavteladze et al. | |
| 6,066,167 A | 5/2000 | Lau et al. | |
| 6,068,655 A | 5/2000 | Seguin et al. | |
| 6,077,296 A | 6/2000 | Shokoohi et al. | |
| 6,093,203 A | 7/2000 | Uflacker | |
| 6,096,071 A | 8/2000 | Yadav | |
| 6,106,548 A * | 8/2000 | Roubin et al. | 623/1.15 |
| 6,117,140 A | 9/2000 | Munsinger | |
| 6,120,522 A | 9/2000 | Vrba et al. | |
| 6,129,738 A | 10/2000 | Lashinski et al. | |
| 6,143,002 A | 11/2000 | Vietmeier | |
| 6,143,016 A * | 11/2000 | Bleam et al. | 606/198 |
| 6,146,415 A | 11/2000 | Fitz | |
| 6,159,238 A | 12/2000 | Killion et al. | |
| 6,159,239 A | 12/2000 | Greenhalgh | |
| 6,165,195 A | 12/2000 | Wilson et al. | |
| 6,179,858 B1 | 1/2001 | Squire et al. | |
| 6,183,509 B1 | 2/2001 | Dibie | |
| 6,197,049 B1 | 3/2001 | Shaolian et al. | |
| 6,203,568 B1 | 3/2001 | Lombardi | |
| 6,210,429 B1 | 4/2001 | Vardi et al. | |
| 6,210,431 B1 | 4/2001 | Power | |
| 6,221,090 B1 | 4/2001 | Wilson | |
| 6,221,098 B1 | 4/2001 | Wilson et al. | |
| 6,228,110 B1 | 5/2001 | Munsinger | |
| 6,231,598 B1 | 5/2001 | Berry et al. | |
| 6,245,100 B1 | 6/2001 | Davila et al. | |
| 6,258,116 B1 | 7/2001 | Hojeibane | |
| 6,258,121 B1 | 7/2001 | Yang et al. | |
| 6,261,316 B1 | 7/2001 | Shaolian et al. | |
| 6,264,682 B1 | 7/2001 | Wilson et al. | |
| 6,264,686 B1 | 7/2001 | Rieu et al. | |
| 6,283,992 B1 | 9/2001 | Hankh et al. | |
| 6,293,966 B1 | 9/2001 | Frantzen | |
| 6,302,893 B1 | 10/2001 | Limon et al. | |
| 6,305,436 B1 | 10/2001 | Andersen et al. | |
| 6,309,412 B1 | 10/2001 | Lau et al. | |
| 6,315,794 B1 | 11/2001 | Richter | |
| 6,322,847 B1 | 11/2001 | Zhong et al. | |
| 6,325,819 B1 | 12/2001 | Pavcnik et al. | |
| 6,325,820 B1 | 12/2001 | Khosravi et al. | |
| 6,330,884 B1 | 12/2001 | Kim | |
| 6,331,186 B1 * | 12/2001 | Wang et al. | 623/1.11 |
| 6,334,871 B1 | 1/2002 | Dor et al. | |
| 6,340,368 B1 | 1/2002 | Verbeck | |
| 6,358,556 B1 | 3/2002 | Ding et al. | |

| | | |
|---|---|---|
| 6,361,544 B1 | 3/2002 | Wilson et al. |
| 6,361,557 B1 | 3/2002 | Gittings et al. |
| 6,375,676 B1 | 4/2002 | Cox |
| 6,391,050 B1 | 5/2002 | Broome |
| 6,391,051 B2 | 5/2002 | Sullivan, III et al. |
| 6,395,017 B1 * | 5/2002 | Dwyer et al. ............... 623/1.11 |
| 6,398,807 B1 | 6/2002 | Chouinard et al. |
| 6,402,777 B1 | 6/2002 | Globerman et al. |
| 6,409,750 B1 | 6/2002 | Hyodoh et al. |
| 6,409,752 B1 | 6/2002 | Boatman et al. |
| 6,409,755 B1 | 6/2002 | Vrba |
| 6,413,269 B1 | 7/2002 | Bui et al. |
| 6,416,542 B1 | 7/2002 | Marcade et al. |
| 6,428,566 B1 | 8/2002 | Holt |
| 6,440,165 B1 | 8/2002 | Richter et al. |
| 6,458,867 B1 * | 10/2002 | Wang et al. ............... 523/105 |
| 6,464,721 B1 | 10/2002 | Marcade et al. |
| 6,471,721 B1 | 10/2002 | Dang |
| 6,475,208 B2 | 11/2002 | Mauch |
| 6,475,236 B1 | 11/2002 | Roubin et al. |
| 6,488,700 B2 | 12/2002 | Klumb et al. |
| 6,491,681 B1 | 12/2002 | Kunis et al. |
| 6,491,938 B2 | 12/2002 | Kunz et al. |
| 6,494,875 B1 | 12/2002 | Mauch |
| 6,497,916 B1 | 12/2002 | Taylor et al. |
| 6,503,271 B2 | 1/2003 | Duerig et al. |
| 6,508,836 B2 | 1/2003 | Wilson et al. |
| 6,514,281 B1 | 2/2003 | Blaeser et al. |
| 6,520,988 B1 | 2/2003 | Colombo et al. |
| 6,527,789 B1 | 3/2003 | Lau et al. |
| 6,533,810 B2 | 3/2003 | Hankh et al. |
| 6,562,063 B1 | 5/2003 | Euteneuer et al. |
| 6,592,615 B1 | 7/2003 | Marcade et al. |
| 6,596,020 B2 | 7/2003 | Vardi et al. |
| 6,610,087 B1 | 8/2003 | Zarbatany et al. |
| 6,613,072 B2 | 9/2003 | Lau et al. |
| 6,613,075 B1 * | 9/2003 | Healy et al. ............... 623/1.11 |
| 6,620,194 B2 | 9/2003 | Ding et al. |
| 6,648,913 B1 | 11/2003 | Vee et al. |
| 6,652,579 B1 | 11/2003 | Cox et al. |
| 6,656,212 B2 | 12/2003 | Ravenscroft et al. |
| 6,660,030 B2 | 12/2003 | Shaolian et al. |
| 6,663,665 B2 | 12/2003 | Shaolian et al. |
| 6,666,883 B1 | 12/2003 | Seguin et al. |
| 6,669,719 B2 | 12/2003 | Wallace et al. |
| 6,689,159 B2 | 2/2004 | Lau et al. |
| 6,692,483 B2 | 2/2004 | Vardi et al. |
| 6,695,875 B2 | 2/2004 | Stelter |
| 6,699,274 B2 | 3/2004 | Stinson |
| 6,702,846 B2 | 3/2004 | Mikus et al. |
| 6,706,062 B2 | 3/2004 | Vardi et al. |
| 6,709,440 B2 | 3/2004 | Callol et al. |
| 6,733,523 B2 | 5/2004 | Shaolian |
| 6,780,174 B2 | 8/2004 | Mauch |
| 6,827,735 B2 | 12/2004 | Greenberg |
| 6,863,685 B2 | 3/2005 | Davila et al. |
| 6,896,699 B2 | 5/2005 | Wilson et al. |
| 6,964,681 B2 | 11/2005 | Murray, III |
| 7,125,419 B2 | 10/2006 | Sequin et al. |
| 7,160,318 B2 | 1/2007 | Greenberg et al. |
| 7,238,197 B2 | 7/2007 | Sequin et al. |
| 7,243,408 B2 | 7/2007 | Vietmeier |
| 7,344,556 B2 | 3/2008 | Seguin et al. |
| 7,686,845 B2 | 3/2010 | Seguin et al. |
| 2001/0004705 A1 | 6/2001 | Killion et al. |
| 2001/0010013 A1 | 7/2001 | Cox et al. |
| 2001/0012943 A1 | 8/2001 | Shaolian et al. |
| 2001/0025195 A1 | 9/2001 | Shaolian et al. |
| 2001/0037138 A1 | 11/2001 | Wilson et al. |
| 2001/0037142 A1 | 11/2001 | Stelter et al. |
| 2001/0044595 A1 | 11/2001 | Reydel et al. |
| 2001/0044622 A1 | 11/2001 | Vardi et al. |
| 2002/0016597 A1 | 2/2002 | Dwyer et al. |
| 2002/0035389 A1 | 3/2002 | Richter et al. |
| 2002/0058984 A1 | 5/2002 | Butaric et al. |
| 2002/0072790 A1 | 6/2002 | McGuckin, Jr. et al. |
| 2002/0107330 A1 | 8/2002 | Pinchuk et al. |
| 2002/0123791 A1 | 9/2002 | Harrison |
| 2002/0143386 A1 | 10/2002 | Davila et al. |
| 2002/0198587 A1 | 12/2002 | Greenberg et al. |
| 2003/0093109 A1 | 5/2003 | Mauch |
| 2003/0114912 A1 | 6/2003 | Seguin et al. |
| 2003/0125791 A1 | 7/2003 | Seguin et al. |
| 2003/0125802 A1 | 7/2003 | Callol et al. |
| 2003/0130720 A1 | 7/2003 | DePalma et al. |
| 2003/0139796 A1 | 7/2003 | Sequin et al. |
| 2003/0139803 A1 | 7/2003 | Sequin et al. |
| 2003/0144724 A1 | 7/2003 | Murray, III |
| 2003/0163188 A1 | 8/2003 | Haverkost et al. |
| 2003/0181973 A1 | 9/2003 | Sahota |
| 2003/0187494 A1 | 10/2003 | Loaldi |
| 2004/0006381 A1 | 1/2004 | Sequin et al. |
| 2004/0098114 A1 | 5/2004 | Wilson et al. |
| 2004/0102838 A1 | 5/2004 | Killion et al. |
| 2005/0049680 A1 | 3/2005 | Fischell et al. |
| 2006/0069421 A1 | 3/2006 | Murray, III |
| 2006/0100685 A1 | 5/2006 | Seguin et al. |
| 2006/0142849 A1 | 6/2006 | Killion et al. |
| 2006/0259136 A1 | 11/2006 | Nguyen et al. |
| 2007/0067011 A1 | 3/2007 | Krolik et al. |
| 2007/0100425 A1 | 5/2007 | Sequin et al. |
| 2008/0046064 A1 | 2/2008 | Sequin et al. |
| 2008/0046072 A1 | 2/2008 | Laborde et al. |
| 2008/0161903 A1 | 7/2008 | Sequin et al. |
| 2010/0256744 A1 | 10/2010 | Laborde et al. |

FOREIGN PATENT DOCUMENTS

| | | |
|---|---|---|
| EP | 0 520 721 A2 | 6/1992 |
| EP | 0 421 729 B1 | 1/1996 |
| EP | 0698380 | 2/1996 |
| EP | 0 941 716 A2 | 9/1999 |
| FR | 2 722 678 | 1/1996 |
| JP | 01299550 A | 12/1989 |
| JP | 3151983 A | 6/1991 |
| JP | 04-064367 A | 2/1992 |
| JP | 6-007454 A | 1/1994 |
| JP | 07308331 A | 11/1995 |
| JP | 11-512635 A | 11/1999 |
| JP | 2001-245886 A | 3/2001 |
| WO | WO 93/13824 | 7/1993 |
| WO | WO 94/12136 A1 | 6/1994 |
| WO | WO 95/21592 | 8/1995 |
| WO | WO 95/32757 | 12/1995 |
| WO | WO 96/14028 | 5/1996 |
| WO | WO 96/29955 | 10/1996 |
| WO | WO 96/34580 A1 | 11/1996 |
| WO | WO 96/37167 A1 | 11/1996 |
| WO | WO 97/07752 | 3/1997 |
| WO | WO 97/12562 A1 | 4/1997 |
| WO | WO 97/46174 | 12/1997 |
| WO | WO 98/36709 A1 | 8/1998 |
| WO | WO 99/15103 | 4/1999 |
| WO | WO 99/37242 | 7/1999 |
| WO | WO 00/44307 | 8/2000 |
| WO | WO 01/39697 A1 | 6/2001 |
| WO | WO 01/60284 | 8/2001 |
| WO | WO 02/060520 A2 | 8/2002 |
| WO | WO 2004/017865 A1 | 3/2004 |
| WO | WO 2004/041126 | 5/2004 |
| WO | WO 2004/043301 | 5/2004 |
| WO | WO 2008/131266 A1 | 10/2008 |

OTHER PUBLICATIONS

Keeley et al., Immediate and Long-Term Results of Elective and Emergent Percutaneous Interventions on Protected and Unprotected Severaly Narrowed Left Main Coronary Arteries, JAAC vol. 83 Jan. 15, 1999, pp. 242-246; © 1999 by Excerpta Medica, Inc.

Maehara et al., Intravascular Ultrasound Assessment of the Stenoses Location and Morphology in the Left Main Coronary Artery in Relation to Anatomic Left Main Length, JAAC vol. 88, Jul. 1, 2001; pp. 1-4, © 2001 by Excerpta Medica, Inc.

Nayak et al., Left Main Coronary Artery Rotation Atherectomy and Stenting, Southern Medical Journal, vol. 93, No. 4, Apr. 2000, pp. 415-423.

Park et al., Stenting of Unprotected Left Main Coronary Artery Stenoses: Immediate and Late Outcomes, JAAC vol. 31, No. 1, Jan.

1998, pp. 37-42, © 1998 by the American College of Cardiology, Published by Elsevier Science Inc.

Tan et al., Long-Term Clinical Outcomes After Unprotected Left Main Trunk Percutaneous Revascularization in 279 Patients, revision accepted Jul. 25, 2001; pp. 1609-1614; © 2001 American Heart Association, Inc.

Yachia, Daniel, Editor; Stenting the Urinary System, © Isis Medical Media Ltd, Oxford; 1998.

U.S. Patent No. 6,068,655 filed Jun. 5, 1997 including prosecution history.

U.S. Patent No. 6,666,883 filed May 30, 2000 including prosecution history.

U.S. Patent No. 7,344,556 filed May 9, 2003 including prosecution history, including but not limited to Restriction Requirement of May 19, 2005, Non-Final Office Action of Sep. 9, 2005, Final Office Action of Mar. 22, 2006, and Non-Final Office Action of Aug. 10, 2006.

U.S. Patent Application Publication No. 2008/0161903 filed Mar. 17, 2008 including prosecution history.

U.S. Patent Application Publication No. 2007/0100425 filed Oct. 24, 2006 including prosecution history.

U.S. Patent Application Publication No. 2006/0100685 filed May 9, 2005 including prosecution history, including but not limited to Non-Final Office Action of Jun. 5, 2008 and Non-Final Office Action of Feb. 12, 2009.

U.S. Patent No. 7,238,197 filed Aug. 20, 2002 including prosecution history, including but not limited to Restriction Requirement of Mar. 31, 2004, Non-Final Office Action of Mar. 22, 2005, Non-Final Office Action of Jan. 5, 2006, and Final Office Action of Jun. 16, 2006.

U.S. Appl. No. 10/292,385, filed Nov. 11, 2002 including prosecution history, including but not limited to Restriction Requirement of Mar. 23, 2004, Non-Final Office Action of May 29, 2007, Final Office Action of Mar. 25, 2008, Non-Final Office Action of Aug. 22, 2008 and Final Office Action of Mar. 19, 2009.

U.S. Appl. No. 10/304,085, filed Nov. 11, 2002 including prosecution history, including but not limited to Restriction Requirement of Mar. 1, 2005, Non-Final Office Action of May 22, 2007, Final Office Action of Mar. 20, 2008, Non-Final Office Action of Jul. 22, 2008, Non-Final Office Action of Mar. 11, 2009 and Final Office Action of Mar. 19, 2009.

U.S. Patent No. 7,344,556 filed May 9, 2003 including prosecution history, including but not limited to Non-Final Office Action of May 19, 2005, Non-Final Office Action of Sep. 9, 2005, Final Office Action of Mar. 22, 2006, and Non-Final Office Action of Aug. 10, 2006.

U.S. Patent Application Publication No. 2008/0046072 filed Apr. 19, 2007 including prosecution history, including but not limited to Restriction Requirement of Nov. 26, 2008 and Non-final Office Action of Feb. 4, 2009.

U.S. Patent No. 7,125,419 filed Oct. 28, 2002 including prosecution history, including but not limited to Restriction Requirement of Jun. 30, 2004, Non-Final Office Action of Dec. 2, 2004, Non-final Office Action of Jun. 23, 2005, and Final Office Action of Oct. 13, 2008.

U.S. Patent Application Publication No. 2008/0046064 filed Jun. 22, 2007 including prosecution history.

International Search Report for International Application No. PCT/EP02/12509, mailed on Sep. 30, 2003, in 4 pages.

International Search Report for International Application No. PCT/US03/35714, mailed on Apr. 19, 2004, in 2 pages.

International Search Report for International Application No. PCT/US03/25988, mailed on Aug. 1, 2004, in 4 pages.

International Search Report for International Application No. PCT/US08/60884, mailed on Sep. 2, 2008, in 1 page.

Supplementary European Search Report for Application No. EP 03768812.4, dated Nov. 27, 2008, in 3 pages.

International Search Report for International App. No. PCT/FR97/00999, mailed on May 11, 1997.

Examination Report of May 21, 2007 for Australian Patent Application No. 2003259932.

Examination Report of Sep. 19, 2007 for Australian Patent Application No. 2002356575.

Examination Report of Jan. 16, 2008 for Australian Patent Application No. 2003291416.

Examination Report of Sep. 11, 2008 for European Patent Application No. 03793137.5.

Examination Report of Jan. 23, 2007 for European Patent Application No. 02808089.3.

Examination Report of Dec. 13, 2007 for European Patent Application No. 02808089.3.

Examination Report of Feb. 5, 2009 for Japanese Patent Application No. 2004-548704.

Foreign Office Action received in Canadian Patent Application No. 2,505,137 of Nov. 12, 2008, in 2 pages.

Japanese Patent Application No. H10-500284 filed Jun. 5, 1997 including Foreign Office Action of Jun. 20, 2006 in 5 pages and Foreign Office Action of Mar. 6, 2007 in 1 page.

European Search Report received in European Application No. 09004690.5 of May 11, 2009 in 7 pages.

Marco, J. et al., Current Approach for Stenting Bifurcation Lesions, Thierry Lefevre, Yves Louvard, Marie-Claude Morice, The Paris Course on Revascularization 2004; 129-54.

* cited by examiner

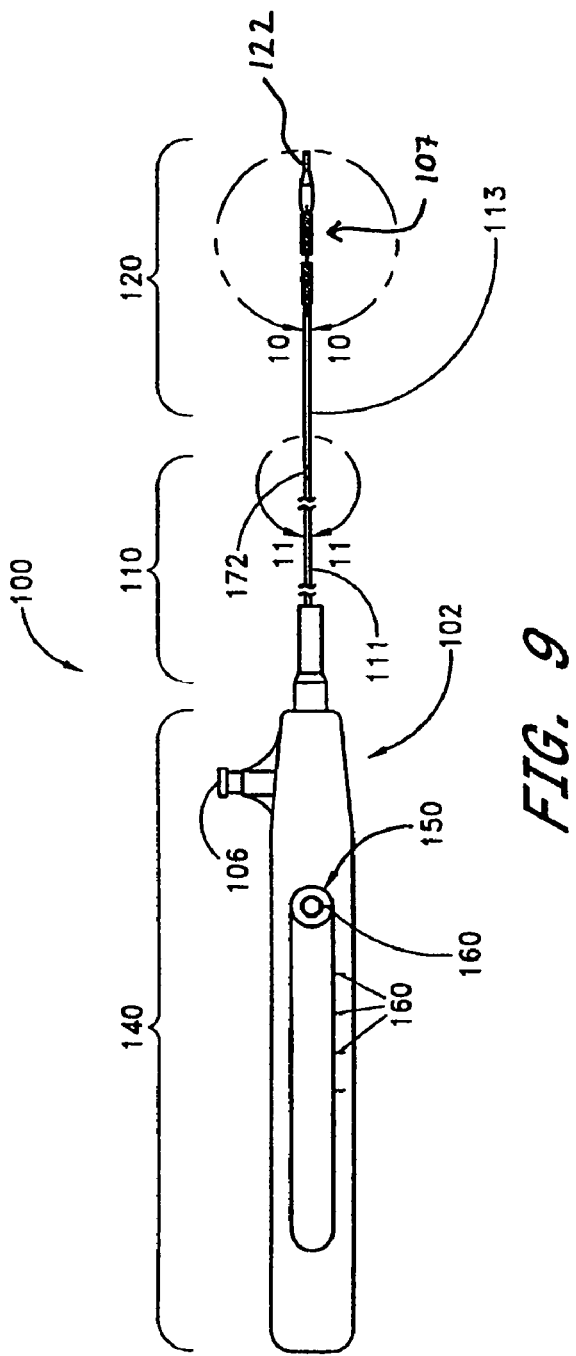
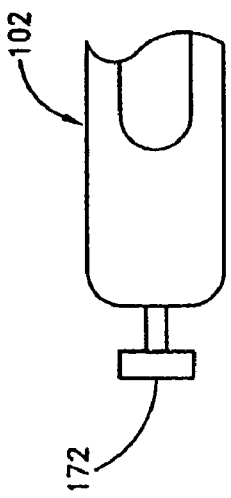
FIG. 9
FIG. 9A

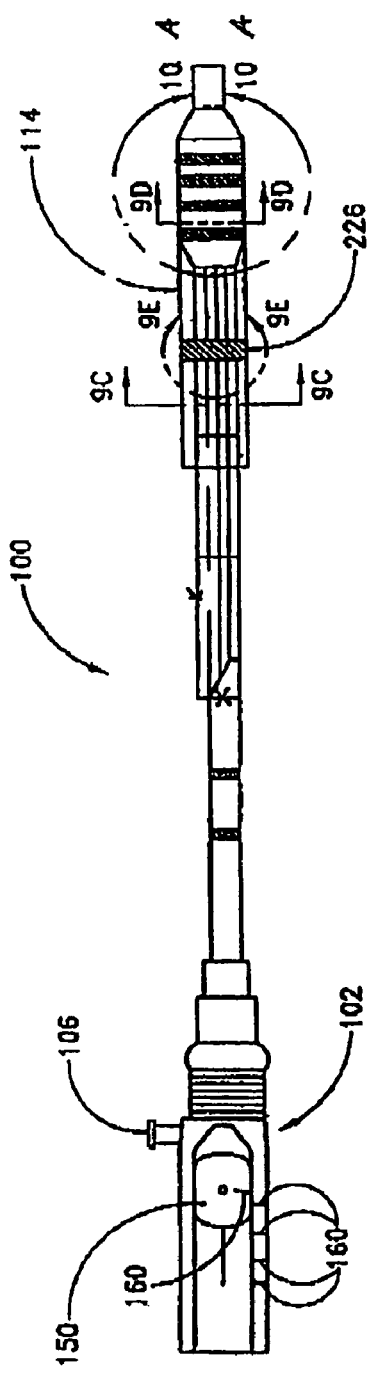
FIG. 9B
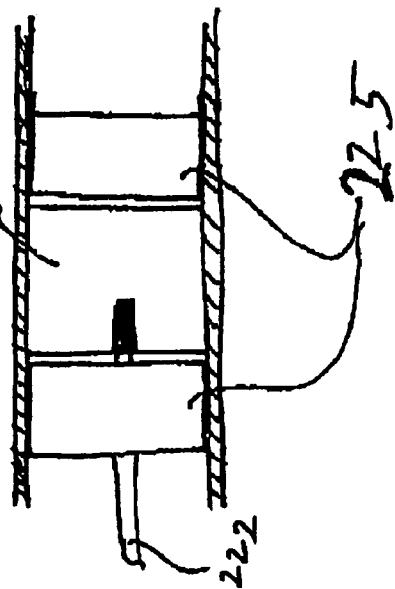
FIG. 9E
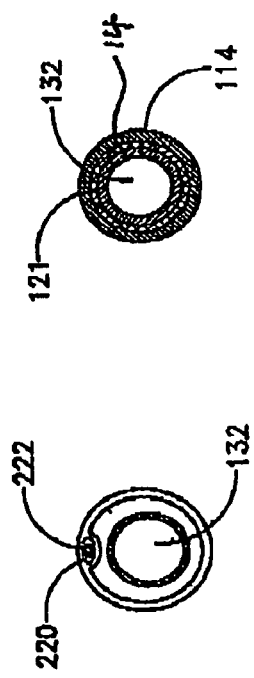
FIG. 9D
FIG. 9C

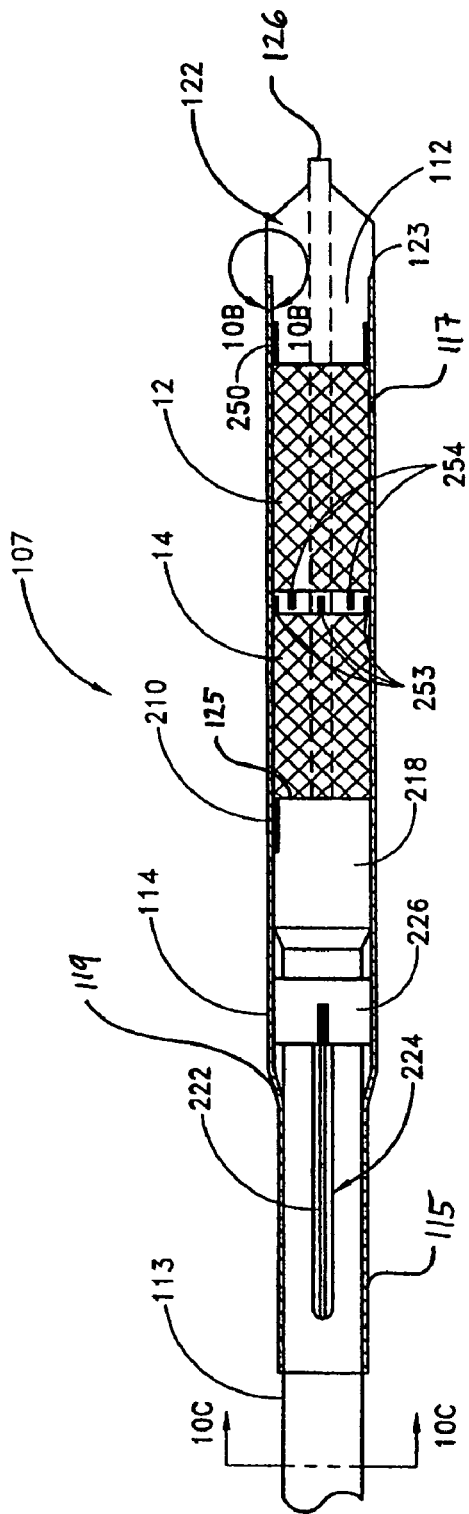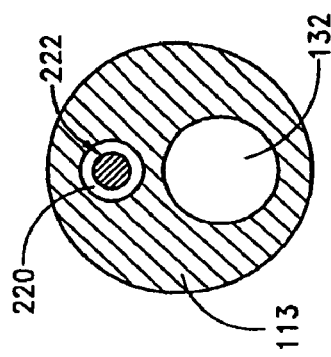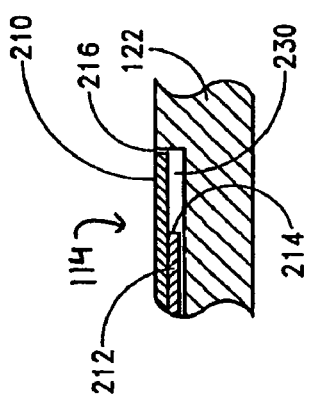
FIG. 10
FIG. 10C
FIG. 10B

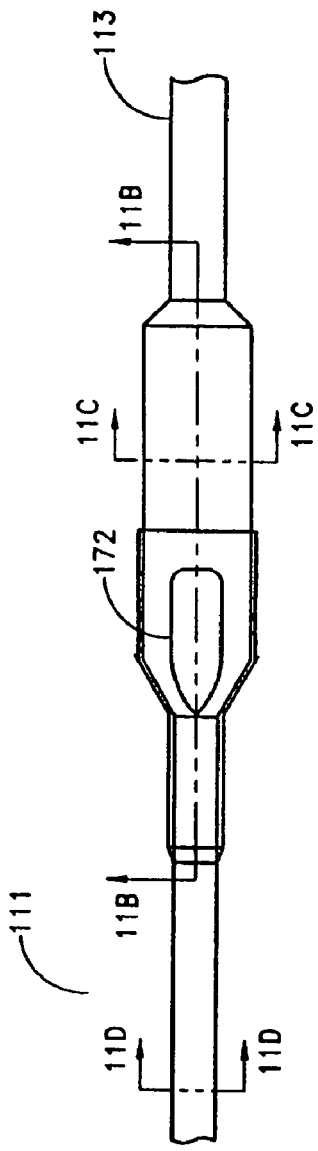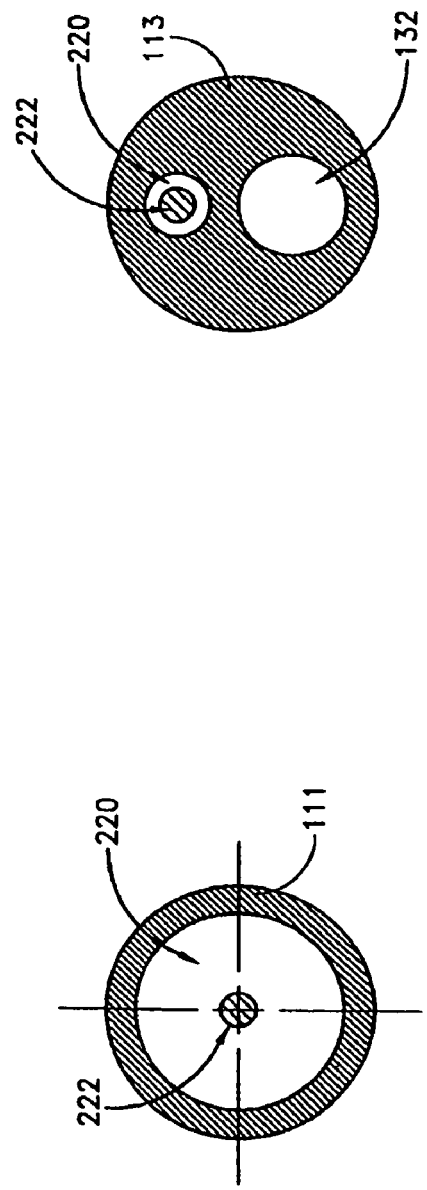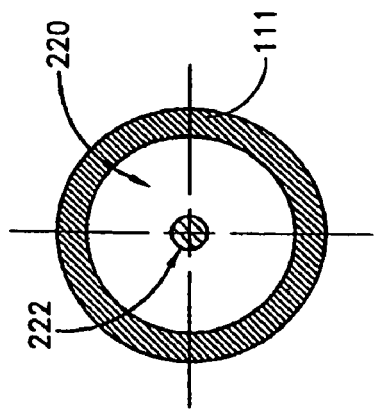

NONCYLINDRICAL STENT DEPLOYMENT SYSTEM FOR TREATING VASCULAR BIFURCATIONS

This is a Divisional of U.S. patent application Ser. No. 10/282,957 filed on Oct. 28, 2002 now U.S. Pat. No. 7,125,419 which is a Continuation of U.S. patent application Ser. No. 10/225,484 filed on Aug. 20, 2002 now U.S. Pat. No. 7,238,197 which is a Continuation-In-Part of U.S. patent application Ser. No. 09/580,597, which was filed on May 30, 2000, now U.S. Pat. No. 6,666,883 the disclosures of which are incorporated in their entirety herein by reference.

BACKGROUND

1. Scope of the Invention

The present invention relates to an apparatus permitting the treatment of bodily conduits, typically blood vessels, in an area of a bifurcation, e.g. in an area where a principal conduit separates into two secondary conduits. It also relates to equipment for positioning this apparatus.

2. Description of the Related Art

It is known to treat rectilinear blood vessel narrowing by means of a radially expandable tubular device, commonly referred to as a stent. This stent is introduced in the unexpanded state into the internal lumen of the vessel, in particular by the percutaneous route, as far as the area of narrowing. Once in place, the stent is expanded in such a way as to support the vessel wall and thus re-establish the appropriate cross section of the vessel.

Stent devices can be made of a non-elastic material, in which case the stent is expanded by an inflatable balloon on which it is engaged. Alternatively, the stent can be self-expanding, e.g. made of an elastic material. A self-expanding stent typically expands spontaneously when withdrawn from a sheath which holds it in a contracted state.

For example, U.S. Pat. Nos. 4,733,065 and 4,806,062 illustrate existing stent devices and corresponding positioning techniques.

A conventional stent is not entirely suitable for the treatment of a narrowing situated in the area of a bifurcation, since its engagement both in the principal conduit and in one of the secondary conduits can cause immediate or delayed occlusion of the other secondary conduit.

It is known to reinforce a vascular bifurcation by means of a stent comprising first and second elements, each formed by helical winding of a metal filament. The first of the two elements has a first part having a diameter corresponding to the diameter of the principal vessel, and a second part having a diameter corresponding to the diameter of a first one of the secondary vessels. The first element is intended to be engaged in the principal vessel and the second element is intended to be engaged in the first secondary vessel. The second element has a diameter corresponding to the diameter of the second secondary vessel. After the first element has been put into place, the second element is then coupled to the first element by engaging one or more of its turns in the turns of the first element.

This equipment permits reinforcement of the bifurcation but appears unsuitable for treating a vascular narrowing or an occlusive lesion, in view of its structure and of the low possibility of radial expansion of its two constituent elements.

Moreover, the shape of the first element does not correspond to the shape of a bifurcation, which has a widened transitional zone between the end of the principal vessel and the ends of the secondary vessels. Thus, this equipment does not make it possible to fully support this wall or to treat a dissection in the area of this wall. Additionally, the separate positioning of these two elements is quite difficult.

SUMMARY OF THE INVENTION

There is provided in accordance with one aspect of the present invention, a method of treating a vascular bifurcation of a main vessel into a first and a second branch vessels. The method comprises the steps of providing a delivery catheter having a stent thereon, the stent having a proximal end and a distal end and being self expandable to a configuration in which the proximal end has a smaller diameter than the distal end. The catheter is positioned such that the stent is at a treatment site within the main vessel, with the distal end adjacent the bifurcation. The stent is deployed in the main vessel such that the distal end communicates with both the first and the second branch vessels.

In one implementation of the invention, the method additionally comprises the step of dilating the treatment site prior to the positioning step. The deploying step may comprise removing a restraint from the stent and permitting the stent to self expand. The method may additionally comprise the step of deploying a second stent in one of the first and second branch vessels.

In one implementation of the invention, the distal end of the stent expands to a diameter that is at least about 105% of the diameter of the proximal end of the stent. In certain applications, the distal end of the stent expands to a diameter that is at least about 110% of the diameter of the proximal end of the stent.

In accordance with another aspect of the present invention, there is provided a deployment system for treating a bifurcation of a main vessel into a first and second branch vessels. The deployment system comprises an elongate flexible body, having a proximal end and a distal end. A tapered stent is carried by the distal end of the body. A releasable restraint for restraining the stent is also carried by the body. The distal end of the stent is larger in diameter than the proximal end of the stent in an unconstrained expanded configuration.

The deployment system may additionally comprise a guidewire lumen extending axially through at least a portion of the flexible body. The guidewire lumen has a proximal access port and a distal access port. In one implementation, the proximal access port is positioned along the flexible body, spaced distally apart from the proximal end. In another implementation, the proximal access port is positioned at the proximal end of the body.

The releasable restraint may comprise an axially moveable control element extending along the length of the flexible body. The releasable restraint may also comprise a tubular sheath, for restraining the stent. The tubular sheath may be attached to an axially moveable pull wire.

In accordance with a further aspect of the present invention, there is provided a method of treating a vascular bifurcation of a main vessel into first and second branch vessels. The method comprises the steps of deploying a substantially cylindrical stent in a first branch vessel which is distal to the bifurcation, and deploying a tapered stent in the main vessel, proximal to the bifurcation. The tapered stent tapers in a distal direction from a smaller proximal diameter to a larger distal diameter which faces the bifurcation.

In accordance with another aspect of the present invention, there is provided a stent deployment catheter. The catheter comprises an elongate flexible tubular body, having a proximal end and a distal end. A noncylindrical, self expandable stent is carried by the distal end. A hand piece is provided on the proximal end. A control is provided on the hand piece, for controllably removing a restraint from the noncylindrical self expandable stent. In one application, the control has a first position for indicating a partial deployment of the stent, and a second position indicating complete deployment of the stent.

All of these embodiments are intended to be within the scope of the present invention herein disclosed. These and other embodiments of the present invention will become readily apparent to those skilled in the art from the following detailed description of the preferred embodiments having reference to the attached figures, the invention not being limited to any particular embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the attached figures, of which:

FIG. 9 is a plan view of a delivery catheter usable to deploy a stent system having certain features and advantages;

FIG. 9A is an alternative embodiment of a proximal handpiece of the delivery catheter of FIG. 9;

FIG. 9B is an alternative embodiment of the delivery catheter of FIG. 9;

FIG. 9C is a section view of a portion of the delivery catheter of FIG. 9 taken through line 9C-9C and specifically showing an alternative pull wire lumen;

FIG. 9D is a section view of a portion of the delivery catheter of FIG. 9 taken through line 9D-9D and specifically showing a retaining band;

FIG. 9E is a detail view of a retraction band retention assembly of the delivery catheter of FIG. 9;

FIG. 10 is a partial cutaway view of a distal portion of the catheter of FIG. 9 including a stent system disposed thereon;

FIG. 10B is a detail view of a distal portion of the outer sheath shown in FIG. 10;

FIG. 10C is a section view taken along the line 10C-10C of FIG. 10;

FIG. 11A is a plan view of a transitional portion of the catheter of FIG. 9;

FIG. 11C is a transverse sectional view of the transitional portion taken along the line 11C-11C of FIG. 11A;

FIG. 11D is a cross sectional view of the proximal shaft taken along the line 11D-11D of FIG. 11A;

DETAILED DESCRIPTION OF THE PREFERRED EMBODIMENT

Figure 3:
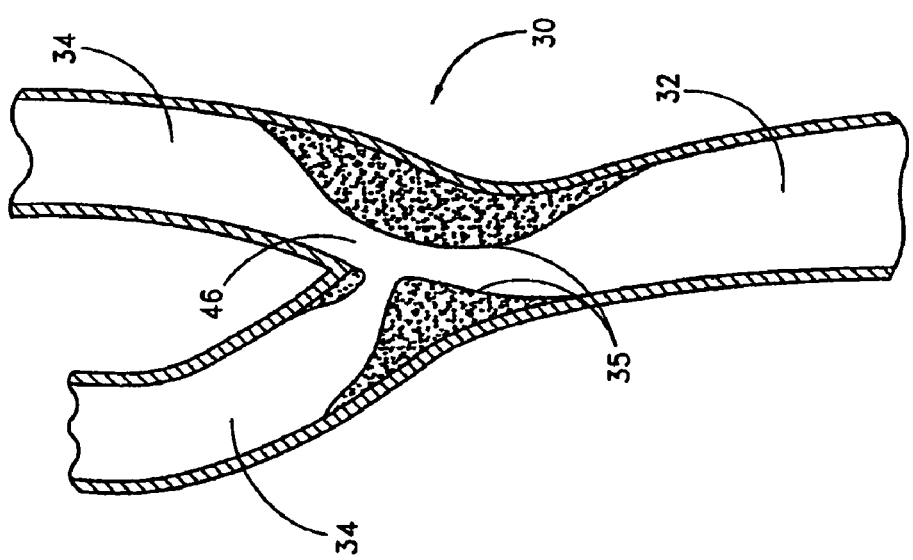
FIG. 3 is a longitudinal sectional view of a bifurcation treatable by the stent system of FIG. 1.

As described above, the attached Figures illustrate a stent system and corresponding delivery system for use in treating vessels (e.g. conduits) within the human body at areas of bifurcations. FIG. 3 shows a bifurcation 30 in which a main conduit or vessel 32 separates into two secondary branch conduits or vessels 34. The stent system generally includes a pair of dissimilar stents specifically designed for use in an area of a bifurcation 30. Such dissimilar stents are then disposed on an elongate catheter for insertion into the human body. The dissimilar stents may be self-expanding or manually expandable such as by a balloon about which the stents may be disposed as will be described in further detail below.

Figures 1, 2:
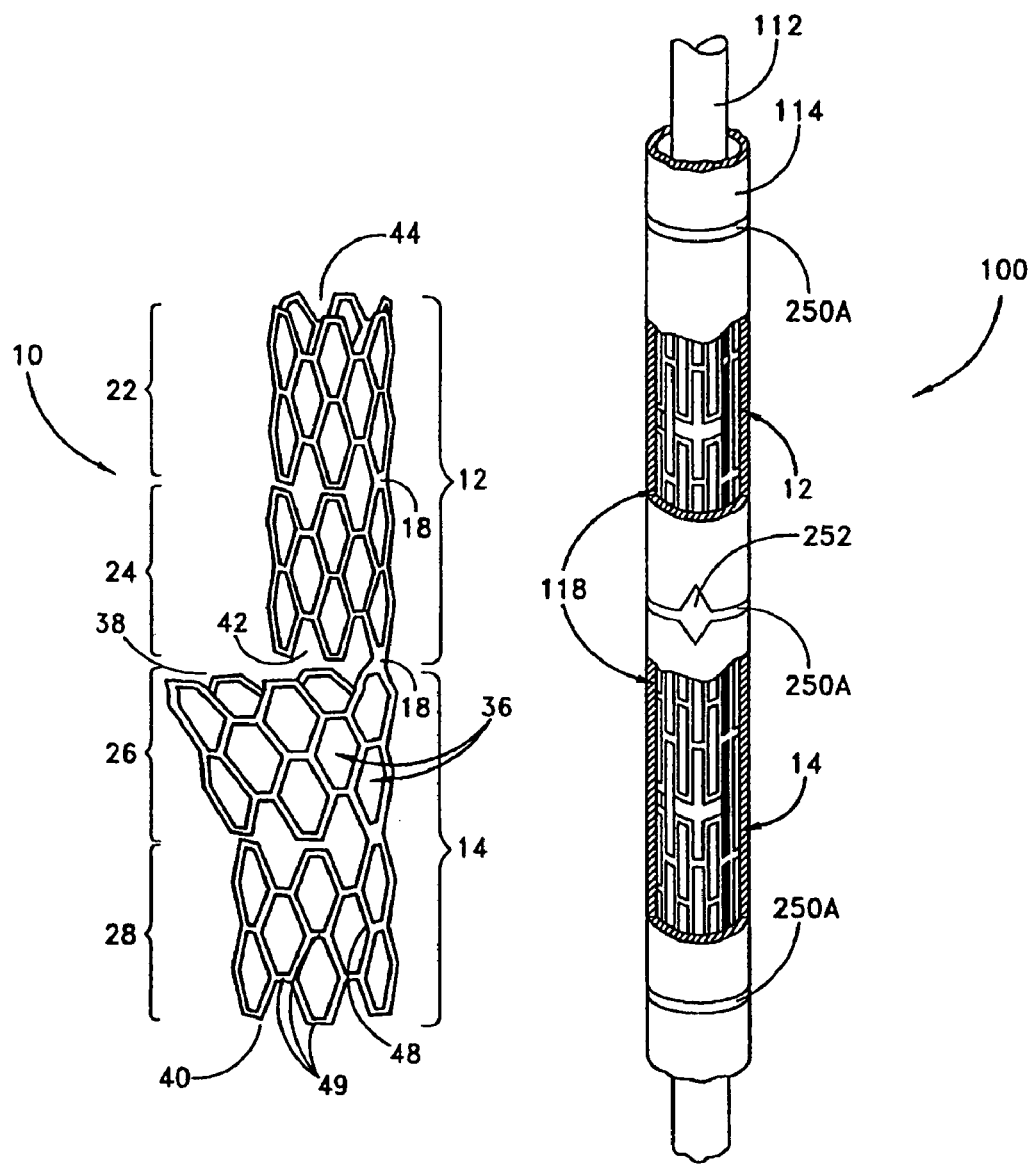
FIG. 1 is a side view of a first embodiment of a stent system shown in an expanded state.
FIG. 2 is a perspective, partial cutaway view of the stent system of FIG. 1 shown in a state of radial contraction, as disposed on a delivery catheter.

FIG. 1 shows one embodiment of an expandable stent system 10 permitting the treatment of bodily conduits in the area of a bifurcation such as that shown. The stent system 10, shown in an expanded state in FIG. 1, generally comprises first 12 and second 14 stent portions which may each be divided into two segments, thus creating four successive segments 22, 24, 26, 28, of meshwork structure. The first stent 12 is generally adapted to be disposed in a branch conduit or vessel 34 of a bifurcation, while the second stent 14 is generally adapted to be disposed in a main vessel 32. If desired, the segments may be connected to one another via one or more bridges of material 18. The stents 12, 14 are generally movable between a contracted position and an expanded position. As will be clear to those skilled in the art, the stents may be self-expanding or balloon-expandable.

According to the illustrated embodiment, the stents 12, 14 generally comprise an expandable mesh structure which includes a plurality of mesh cells 36. The mesh cells 36 of these segments are in one embodiment elongated in the longitudinal direction of the stents 12, 14 and have in each case a substantially hexagonal shape in the embodiment shown. Those skilled in the art will recognize that the mesh used to form the stent segments 22, 24, 26, and 28 may comprise a variety of other shapes known to be suitable for use in stents. For example a suitable stent may comprise mesh with repeating quadrilateral shapes, octagonal shapes, a series of curvatures, or any variety of shapes such that the stent is expandable to substantially hold a vessel or conduit at an enlarged inner diameter.

The first stent 12 may be divided into two segments 22 and 24 which may be identical to each other and typically have a tubular shape with a diameter which is substantially greater than the diameter of one of the secondary branch conduits 34. Those skilled in the art will recognize that the first stent may comprise a variety of shapes such that it functions as described herein. The first stent 12 may be expandable to a substantially cylindrical shape having a constant diameter along its length. The first stent 12 may comprise a range of lengths depending on the specific desired location of placement. For example, the length of the first stent 12 will typically be between about 1 and about 4 centimeters as desired.

The second stent 14 is preferably adapted to be deployed in close proximity to the first stent 12, and may also be divided into upper 26 and lower 28 segments. The lower segment 28 of the second stent 14 typically has a tubular cross-sectional shape and has an expanded diameter which is substantially greater than the diameter of the principal conduit 32 (FIG. 3). The upper segment 26 of the second stent 14 preferably comprises a larger diameter at its distal (upper) end 38 than at its proximal (lower) end 40. In one embodiment the upper segment of the second stent portion comprises a substantially conical shape. In an alternative embodiment, the second stent 14 may be tapered radially outward along its entire length in the distal direction. In either embodiment however, the expanded diameter of the distal end 38 of the second stent 14 is preferably substantially larger than the expanded diameter of the proximal end 42 of the first stent 12. For example, the distal end 38 of the second stent 14 may expand to a diameter that is at least about 105%, and preferably at least about 110%, and in some embodiments as much as 120% or more, of the diameter of the proximal end 42 of the first stent 12. The second stent 14 may comprise a range of lengths depending on the specific desired location of placement. For example, the second stent 14 will typically be between 1 and 4 centimeters as desired.

In its expanded state, as shown in FIG. 1, the upper segment 26 of the second stent 14 typically has mesh cells 36 whose width increases progressively, compared to that of the meshes of the lower segment 28, on the one hand in the longitudinal sense of the dual stent device 10, in the direction of the distal end 38 of the second stent 14, and, on the other hand, in the transverse sense of the second stent 14, in the direction of a generatrix diametrically opposite that located in the continuation of the bridge 18. Alternatively stated, the upper segment 26 of the second stent 14 preferably comprises a mesh with multiple cellular shapes 36 which may have larger dimensions at a distal end 38 of the stent 14 than those at the proximal end 40 such that the second stent 14 expands to a substantially funnel shape.

In the embodiment shown, this increase in the width of the mesh cells 36 results from an increase in the length of the edges 48 of the mesh cells 36 disposed longitudinally, as well as an increase in the angle formed between two facing edges 48.

This segment 26 thus may have a truncated shape with an axis which is oblique in relation to the longitudinal axis of the first stent 12 when expanded. This shape, for example, corresponds to the shape of the bifurcation shown in the area of the widened transitional zone 46 (FIG. 3) which separates the end of the principal conduit 32 from the ends of the secondary conduits 34. In a preferred embodiment, the second stent 14 is placed in close proximity to the first stent 12. For example, the distal end 38 of the second stent 14 is preferably placed within a distance of about 4 mm of the distal end 42 of the first stent 12, more preferably this distance is less than about 2 mm, and most preferably the stents are placed within 1 mm of one another.

In the embodiment shown in FIG. 1, the distance between first and second stents 12, 14 is held substantially fixed by the provision of a bridge 18 between them. Bridges 18 may be provided to join the first and second stents 12, 14 to one another and/or to join the upper and lower segments 22, 24 and 26, 28 of each stent 12 and 14 together. If present, the bridges 18 may connect the adjacent ends of the segments 22, 24 and 26, 28 and typically have a small width, so that they can undergo a certain flexion, making it possible to orient these segments in relation to one another, in particular the lower segment 24 of the first stent 12 in relation to the upper segment 26 of the second stent 14.

In addition, in other embodiments, the bridges 18 could be integral with one of the connected segments and separately connected, such as by welding, to the other connected segment. For example, the bridge 18 which connects the first and second stents 12, 14 could be integral with the upper segment 26 of the second stent 14 and connected to lower segment 24 of the first segment 26. Alternatively, the bridge 18 could be integral with the lower segment 24 of the first stent 12 and connected to the upper segment 26 of the second stent 14.

In yet other embodiments, bridges 18 could be separate pieces of materials which are separately connected to segments 22, 24, 26, 28 such as by welding, adhesion, or other bonding method. In all of these embodiments, the first stent 12 can be made from different pieces of material than the second stent 14. A tube from which the first stent 12 may be made (e.g. by laser cutting techniques) may comprise a smaller diameter than a tube from which the second stent 14 may be made. The respective tubes may or may not be made of the same material. Alternatively, the first and second stent may be formed from a single piece of material.

When the segments 26 and 28 of the second stent 14 are made from tubes of a smaller diameter than the segments 22 and 24 of the first stent 12, the radial force of the first stent segments 22 and 24 is larger than the radial force of the second stent segments 26 and 28, especially at larger cross sections.

Accordingly, bridges 18 can be made from one of these tubes, and thus be integral with segments 22 and 24 or segments 26 and 28. Alternatively, the bridges 18 can be separate pieces of material.

In further embodiments, bridges 18 are omitted such that the individual segments are spaced as desired during installation and use. These individual segments are still delivered and implanted in the same core and sheath assembly.

The bridges 18 between two consecutive segments could be greater or smaller in number than six, and they could have a shape other than an omega shape, permitting their multidirectional elasticity, and in particular a V shape or W shape.

Figure 8:
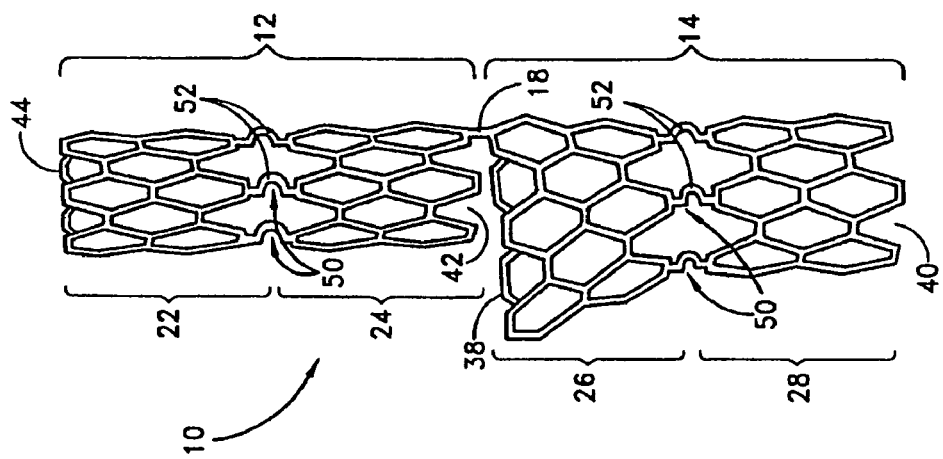
FIG. 8 is a side view of a stent system according to a second embodiment shown in an expanded state.

For example, FIG. 8 shows an alternative embodiment of the stent system 10 with first 12 and second 14 stents shown in their unconstrained, expanded states. According to this embodiment, each stent 12, 14 may be divided into two segments 22, 24 and 26, 28 and may include one or more flexible bridges 18 connecting the first 12 and second stents 14 to one another. In this embodiment, the two consecutive segments 22, 24 and 26, 28 of the first and second stents 12 and 14, are connected by a plurality (e.g. six) omega-shaped bridges 50. The curved central part 52 of these bridges 50 may have a multidirectional elasticity permitting the appropriate longitudinal orientation of the various segments in relation to one another. The advantage of these bridges 50 is that they provide the stent with longitudinal continuity, which facilitates the passage of the stent system into a highly curved zone and which eliminates the need to reduce this curvature, (which may be dangerous in the cases of arteriosclerosis).

Thus, the stent system 10 of FIG. 8 can comprise several segments 22, 24, 26, 28 placed one after the other, in order to ensure supplementary support and, if need be, to increase the hold of the stents in the bifurcation 30. The upper segment 26 of the second stent 14 could have an axis coincident with the longitudinal axis of the first stent, and not oblique in relation to this axis, if such is rendered necessary by the anatomy of the bifurcation which is to be treated.

Alternatively, the lower segment 24 of the first stent 12 could itself have, in the expanded state, a widened shape similar to that of the second stent and corresponding to the shape of the widened connecting zone (increasing diameter in the proximal direction) by which, in certain bifurcations, the secondary conduits 34 are connected to the widened transition zone 46. Thus, the lower segment 24 of the first stent 12, or the entire first stent 12 may have a first diameter at its distal end, and a second, larger diameter at its proximal end with a linear or progressive curve (flared) taper in between. According to this embodiment, this segment 24 would thus have a shape corresponding to the shape of this widened connecting zone, and would ensure perfect support thereof.

One method of making a self-expanding stent is by appropriate cutting of a sheet of nickel/titanium alloy (for example, an alloy known by the name NITINOL may appropriately be used) into a basic shape, then rolling the resulting blank into a tubular form. The blank may be held in a cylindrical or frustroconical form by welding the opposing edges of this blank which come into proximity with each other. The stent (s) may also be formed by laser cutting from metal tube stock as is known in the art. Alternatively, a stent may be formed by selectively bending and forming a suitable cylindrical or non-cylindrical tubular shape from a single or multiple wires, or thin strip of a suitable elastic material. Those skilled in the art will understand that many methods and materials are available for forming stents, only some of which are described herein.

Some Nickel Titanium alloys are malleable at a temperature of the order of 10° C. but can recover a neutral shape at a temperature substantially corresponding to that of the human body. FIG. 2 shows the stent system 10 disposed on a delivery catheter in a state of radial contraction. In one embodiment, a self-expanding stent may be contracted by cooling its constituent material of nickel-titanium or other shape-memory alloy to a temperature below its transformation temperature. The stent may later be expanded by exposing it to a temperature above the transformation temperature. In the present use, a shape-memory alloy with a transformation temperature at or below normal body temperature may be used. Those skilled in the art will recognize that a self-expanding stent made of a substantially elastic material may also be mechanically contracted from its expanded shape by applying a radial compressive force. The stent may then be allowed to expand under the influence of the material's own elasticity. Nickel titanium and other alloys such as such as Silver-Cadmium (Ag—Cd), Gold-Cadmium (Au—Cd) and Iron-Platinum ($Fe_3$—Pt), to name but a few offer desirable superelastic qualities within a specific temperature range.

In one embodiment, the contraction of a stent may cause the mesh cell edges 48 to pivot in relation to the transverse edges 49 of the mesh cells 36 in such a way that the mesh cells 36 have, in this state of contraction, a substantially rectangular shape. Those skilled in the art will recognize that other materials and methods of manufacturing may be employed to create a suitable self-expanding stent.

Alternatively, the stents used may be manually expandable by use of an inflatable dilatation balloon with or without perfusion as will be discussed further below. Many methods of making balloon-expandable stents are known to those skilled in the art. Balloon expandable stents may be made of a variety of bio-compatible materials having desirable mechanical properties such as stainless steel and titanium alloys. Balloon-expandable stents preferably have sufficient radial stiffness in their expanded state that they will hold the vessel wall at the desired diameter. In the case of a balloon-expandable second stent 14, the balloon on which the second stent 14 is disposed may be specifically adapted to conform to the desired shape of the second stent 14. Specifically, such a balloon will preferably have a larger diameter at a distal end than at a proximal end.

The present discussion thus provides a pair of dissimilar stents permitting the treatment of a pathological condition in the area of a bifurcation 30. This system has the many advantages indicated above, in particular those of ensuring a perfect support of the vessel wall and of being relatively simple to position.

For the sake of simplification, the segment which has, in the unconstrained expanded state, a cross section substantially greater than the cross section of one of the secondary conduits will be referred to hereinafter as the "secondary segment", while the segment which has, in the expanded state, a truncated shape will be referred to hereinafter as the "truncated segment."

The secondary segment is intended to be introduced into the secondary conduit in the contracted state and when expanded will preferably bear against the wall of the conduit. This expansion not only makes it possible to treat a narrowing or a dissection situated in the area of the conduit, but also to ensure perfect immobilization of the apparatus in the conduit.

In this position, the truncated segment bears against the wall of the conduit delimiting the widened transitional zone of the bifurcation, which it is able to support fully. A narrowing or a dissection occurring at this site can thus be treated by means of this apparatus, with uniform support of the vascular wall, and thus without risk of this wall being damaged.

The two segments may be adapted to orient themselves suitably in relation to each other upon their expansion.

Advantageously, at least the truncated segment may be covered by a membrane (for example, Dacron® or ePTFE) which gives it impermeability in a radial direction. This membrane makes it possible to trap between it and the wall of the conduit, the particles which may originate from the lesion being treated, such as arteriosclerotic particles or cellular agglomerates, thus avoiding the migration of these particles in the body. Thus, the apparatus can additionally permit treatment of an aneurysm by guiding the liquid through the bifurcation and thereby preventing stressing of the wall forming the aneurysm.

The segments can be made from tubes of material of a different diameter, as discussed above, with the tube for the truncated segment having a larger diameter than the tube for the secondary segment. The tubes may be made from the same material. The use of tubes of different diameters can result in the truncated segment having a larger radial force, especially at larger diameters.

The apparatus can comprise several secondary segments, placed one after the other, to ensure supplementary support of the wall of the secondary conduit and, if need be, to increase the anchoring force of the stent in the bifurcation. To this same end, the apparatus can comprise, on that side of the truncated segment directed toward the principal conduit, at least one radially expandable segment having, in the expanded state, a cross section which is substantially greater than the cross section of the principal conduit.

These various supplementary segments may or may not be connected to each other and to the two aforementioned segments by means of flexible links, such as those indicated above.

The flexible links can be integral with one of the segments and separately connected to the other segment, or the flexible links can be separate pieces of material separately connected to both segments, such as by welding.

Preferably, the flexible link between two consecutive segments is made up of one or more bridges of material connecting the two adjacent ends of these two segments. Said bridge or bridges are advantageously made of the same material as that forming the segments.

Each segment may have a meshwork structure, the meshes being elongated in the longitudinal direction of the stent, and each one having a substantially hexagonal shape; the meshes of the truncated segment may have a width which increases progressively in the longitudinal sense of the stent, in the direction of the end of this segment having the greatest cross section in the expanded state.

This increase in the width of the meshes is the result of an increase in the length of the edges of the meshes disposed longitudinally and/or an increase in the angle formed between two facing edges of the same mesh.

In addition, the truncated segment can have an axis not coincident with the longitudinal axis of the secondary segment, but oblique in relation to this axis, in order to be adapted optimally to the anatomy of the bifurcation which is to be treated. In this case, the widths of the meshes of the truncated segment also increase progressively, in the transverse sense of the stent, in the direction of a generatrix diametrically opposite that located in the continuation of the bridge connecting this segment to the adjacent segment.

The apparatus can be made of a metal with shape memory, which becomes malleable, without elasticity, at a temperature markedly lower than that of the human body, in order to permit retraction of the apparatus upon itself, and to allow it to recover its neutral shape at a temperature substantially corresponding to that of the human body. This metal may be a nickel/titanium alloy known by the name NITINOL.

The deployment catheter for positioning the stent or stents comprises means for positioning the stents and means for permitting the expansion of the stents when the latter are in place. These means can comprise a catheter having a removable sheath in which the stent is placed in the contracted state, when this stent is made of an elastic material, or a support core comprising an inflatable balloon on which the stent is placed, when this stent is made of a nonelastic material.

In either case, this equipment comprises, according to the invention, means with which it is possible to identify and access, through the body of the patient, the longitudinal location of the truncated segment, so that the latter can be correctly positioned in the area of the widened zone of the bifurcation.

In the case where the expansion of this same segment is not uniform in relation to the axis of the stent, the equipment additionally comprises means with which it is possible to identify, through the body of the patient, the angular orientation of the stent in relation to the bifurcation to be treated, so that the part of this segment having the greatest expansion can be placed in a suitable manner in relation to the bifurcation.

Referring to FIG. 9, the stent system is generally deployed using an elongate flexible stent deployment catheter 100. Although primarily described in the context of a multiple stent placement catheter without additional functional capabilities, the stent deployment catheter described herein can readily be modified to incorporate additional features such as an angioplasty balloon or balloons, with or without perfusion conduits, radiation or drug delivery capabilities, or stent sizing features, or any combination of these features, as will be readily apparent to one of skill in the art in view of the disclosure herein.

The elongate delivery catheter 100 generally includes a proximal end assembly 102, a proximal shaft section 110 including a tubular body 111, a distal shaft section 120 including a distal tubular body 113, and a distal end assembly 107. The proximal end 102 may include a handpiece 140, having one or more hemostatic valves and/or access ports 106, such as for the infusion of drugs, contrast media or inflation media in a balloon expandable stent embodiment, as will be understood by those of skill in the art. In addition, a proximal guidewire port 172 may be provided on the handpiece 140 in an over the wire embodiment (see FIG. 9A). The handpiece 140 disposed at the proximal end of the catheter 100 may also be adapted to control deployment of the stents disposed on the catheter distal end 104 as will be discussed.

The length of the catheter depends upon the desired application. For example, lengths in the area of about 120 cm to about 140 cm are typical for use in coronary applications reached from a femoral artery access. Intracranial or lower carotid artery applications may call for a different catheter shaft length depending upon the vascular access site, as will be apparent to those of skill in the art.

The catheter 100 preferably has as small an outside diameter as possible to minimize the overall outside diameter (e.g. crossing profile) of the delivery catheter, while at the same time providing sufficient column strength to permit distal transluminal advancement of the tapered tip 122. The catheter 100 also preferably has sufficient column strength to allow an outer, axially moveable sheath 114 to be proximally retracted relative to the central core 112 in order to expose the stents 118. The delivery catheter 100 may be provided in either "over-the-wire" or "rapid exchange" types as will be discussed further below, and as will generally be understood by those skilled in the art.

In a catheter intended for peripheral vascular applications, the outer sheath 114 will typically have an outside diameter within the range of from about 0.065 inches to about 0.092 inches. In coronary vascular applications, the outer sheath 114 may have an outside diameter with the range of from about 0.039 inches to about 0.065. Diameters outside of the preferred ranges may also be used, provided that the functional consequences of the diameter are acceptable for the intended purpose of the catheter. For example, the lower limit of the diameter for any portion of catheter 100 in a given application will be a function of the number of guidewire, pullwire or other functional lumen contained in the catheter, together with the acceptable minimum flow rate of dilatation fluid, contrast media or drugs to be delivered through the catheter and minimum contracted stent diameter.

The ability of the catheter 100 to transmit torque may also be desirable, such as to avoid kinking upon rotation, to assist in steering, and in embodiments having an asymmetrical distal end on the proximal stent 14. The catheter 100 may be provided with any of a variety of torque and/or column strength enhancing structures, for example, axially extending stiffening wires, spiral wrapped support layers, or braided or woven reinforcement filaments which may be built into or layered on the catheter 100. See, for example, U.S. Pat. No. 5,891,114 to Chien, et al., the disclosure of which is incorporated in its entirety herein by reference.

Referring to FIG. 11D, there is illustrated a cross-sectional view through the proximal section 106 of the catheter shaft 100 of FIG. 9. The embodiment shown in FIG. 11D represents a rapid exchange embodiment, and may comprise a single or multiple lumen extrusion or a hypotube including a pull wire lumen 220. In an over-the-wire embodiment, the proximal section 106 additionally comprises a proximal extension of a guidewire lumen 132 and a pull wire lumen 220. The proximal tube 111 may also comprise an inflation lumen in a balloon catheter embodiment as will be understood by those skilled in the art.

Figure 10A:
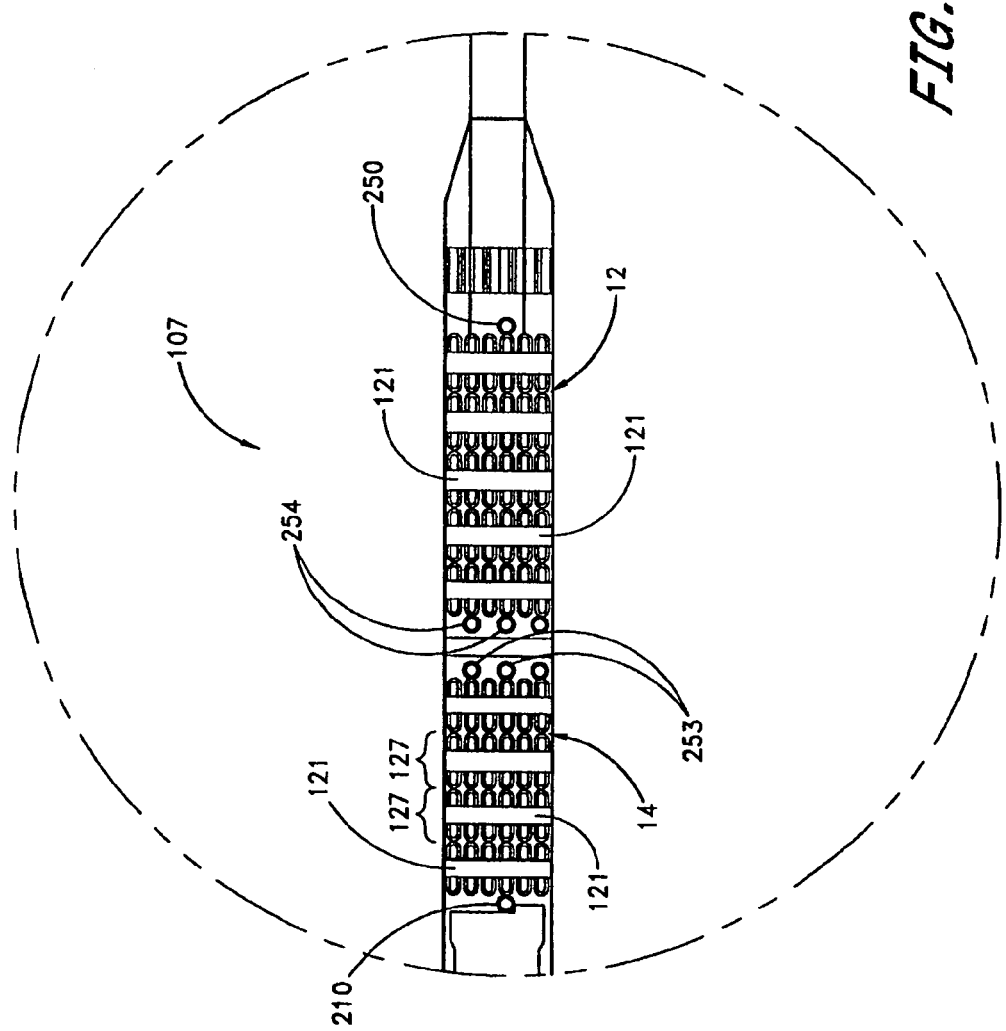
FIG. 10A is an alternative embodiment of a distal end assembly of the delivery catheter of FIG. 9B.
Figure 12:
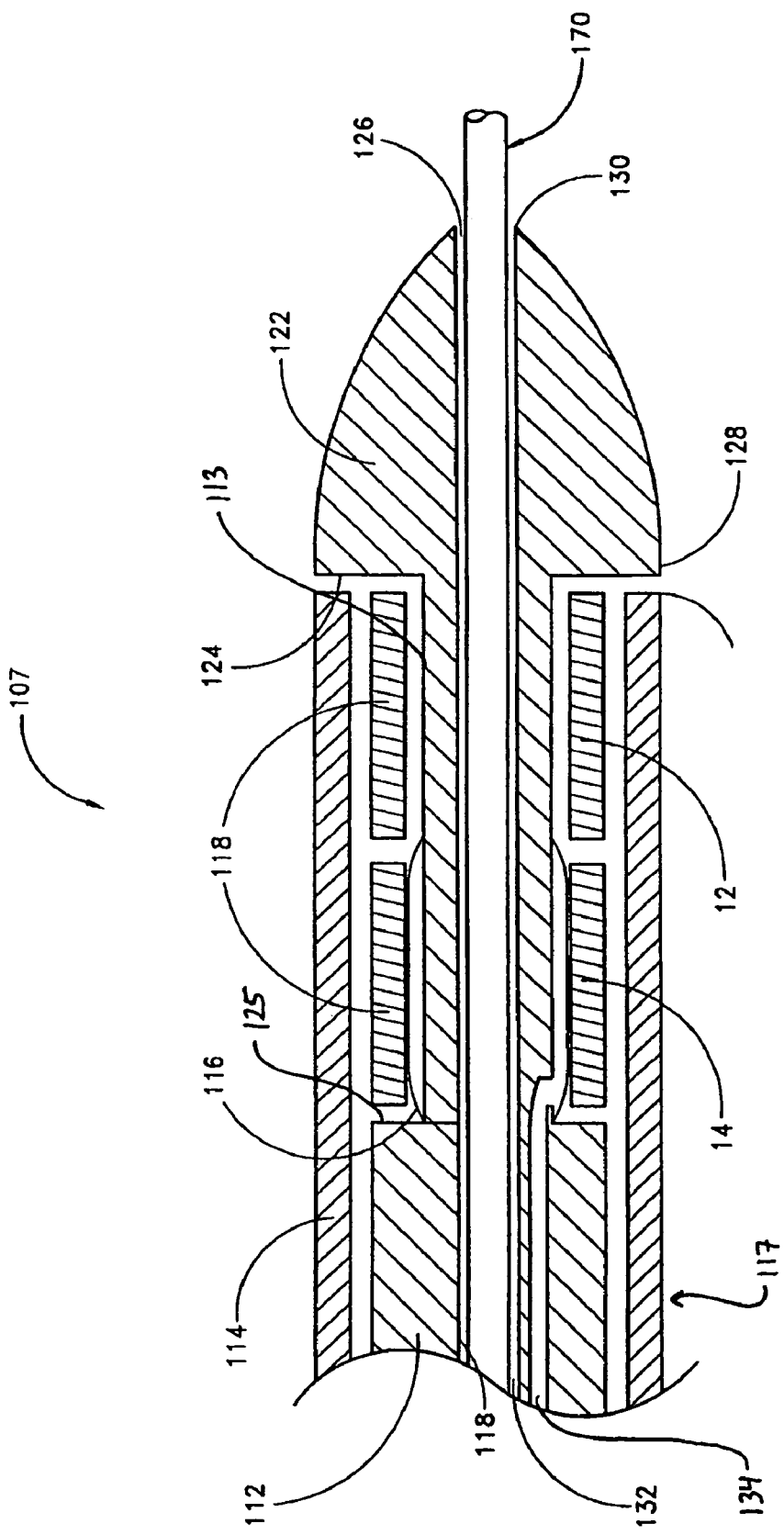
FIG. 12 is a side section view of a distal portion of an embodiment of a delivery catheter having certain features and advantages.
Figure 14:
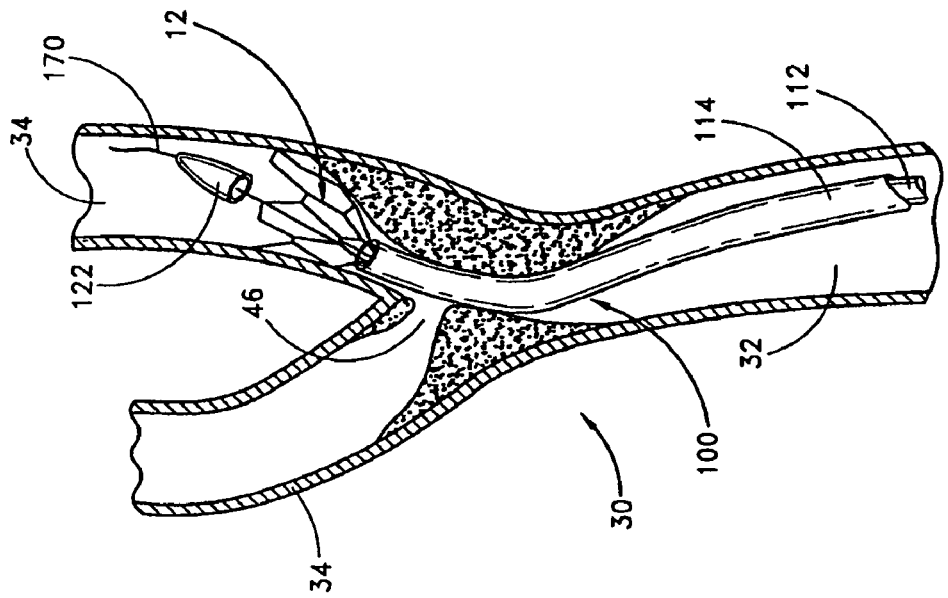
FIG. 14 is a section view of a bifurcation showing a first stent in a partially deployed state.
Figure 13:
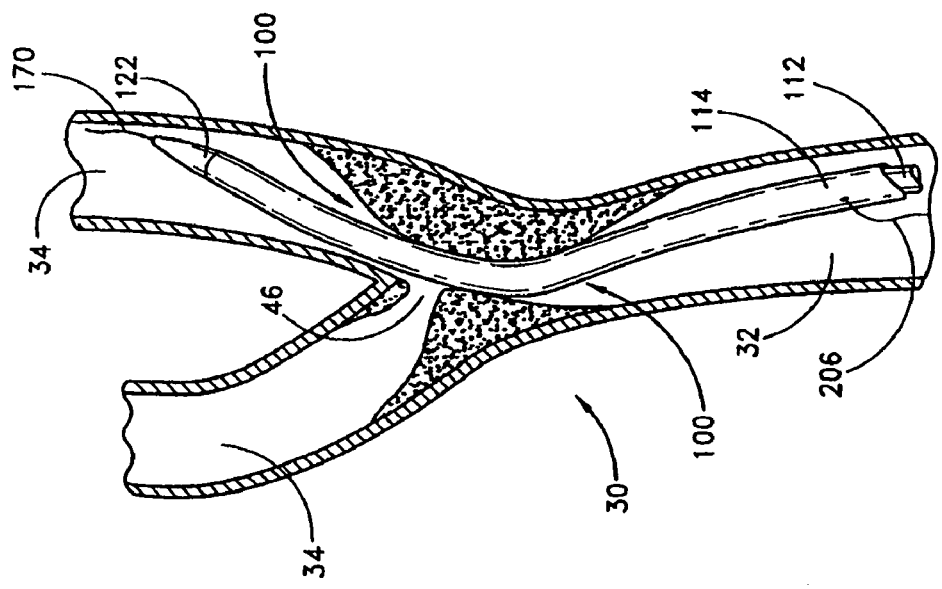
FIG. 13 is a section view of a bifurcation showing an embodiment of a delivery catheter positioned therein.

At the distal end 107, the catheter is adapted to retain and deploy one or more stents within a conduit of a human body. With reference to FIGS. 10A and 12, the distal end assembly 107 of the delivery catheter 100 generally comprises an inner core 112, an axially moveable outer sheath 114, and optionally one or more inflatable balloons 116 (FIG. 12). The inner core 112 is preferably a thin-walled tube at least partially designed to track over a guidewire, such as a standard 0.014 inch guidewire. The outer sheath 114 preferably extends along at least a distal portion 120 of the central core 112 on which the stents 118 are preferably disposed.

The outer sheath 114 may extend over a substantial length of the catheter 100, or may comprise a relatively short length, distal to the proximal guidewire access port 172 as will be discussed. In general, the outer sheath 114 is between about 5 and about 25 cm long.

Referring to FIG. 10, the illustrated outer sheath 114 comprises a proximal section 115, a distal section 117 and a transition 119. The proximal section 115 has an inside diameter which is slightly greater than the outside diameter of the tubular body 113. This enables the proximal section 115 to be slideably carried by the tubular body 113. Although the outer sheath 114 may be constructed having a uniform outside diameter throughout its length, the illustrated outer sheath 114 steps up in diameter at a transition 119. The inside diameter of the distal section 117 of outer sheath 114 is dimensioned to slideably capture the one or more stents as described elsewhere herein. In a stepped diameter embodiment such as that illustrated in FIG. 10, the axial length of the distal section 117 from the transition 119 to the distal end is preferably sufficient to cover the stent or stents carried by the catheter 100. Thus, the distal section 117 in a two stent embodiment is generally at least about 3 cm and often within the range of from about 5 cm to about 10 cm in length. The axial length of the proximal section 115 can be varied considerably, depending upon the desired performance characteristics. For example, proximal section 115 may be as short as one or two centimeters, or up to as long as the entire length of the catheter. In the illustrated embodiment, the proximal section 115 is generally within the range of from about 5 cm to about 15 cm long.

The outer sheath 114 and inner core 112 may be produced in accordance with any of a variety of known techniques for manufacturing rapid exchange or over the wire catheter bodies, such as by extrusion of appropriate biocompatible polymeric materials. Known materials for this application include high and medium density polyethylenes, polytetrafluoroethylene, nylons, PEBAX, PEEK, and a variety of others such as those disclosed in U.S. Pat. No. 5,499,973 to Saab, the disclosure of which is incorporated in its entirety herein by reference. Alternatively, at least a proximal portion or all of the length of central core 112 and/or outer sheath 114 may comprise a metal or polymeric spring coil, solid walled hypodermic needle tubing, or braided reinforced wall, as is understood in the catheter and guidewire arts.

The distal portion 117 of outer sheath 114 is positioned concentrically over the stents 118 in order to hold them in their contracted state. As such, the distal portion 117 of the outer sheath 114 is one form of a releasable restraint. The releasable restraint preferably comprises sufficient radial strength that it can resist deformation under the radial outward bias of a self-expanding stent. The distal portion 117 of the outer sheath 114 may comprise a variety of structures, including a spring coil, solid walled hypodermic needle tubing, banded, or braided reinforced wall to add radial strength as well as column strength to that portion of the outer sheath 114. Alternatively, the releasable restraint may comprise other elements such as water soluble adhesives or other materials such that once the stents are exposed to the fluid environment and/or the temperature of the blood stream, the restraint material will dissolve, thus releasing the self-expandable stents. A wide variety of biomaterials which are absorbable in an aqueous environment over different time intervals are known including a variety of compounds in the polyglycolic acid family, as will be understood by those of skill in the art. In yet another embodiment, a releasable restraint may comprise a plurality of longitudinal axial members disposed about the circumference of the stents. According to this embodiment anywhere from one to ten or more axial members may be used to provide a releasable restraint. The axial members may comprise cylindrical rods, flat or curved bars, or any other shape determined to be suitable.

In some situations, self expanding stents will tend to embed themselves in the inner wall of the outer sheath 114 over time. As illustrated in FIGS. 9D and 10A, a plurality of expansion limiting bands 121 may be provided to surround sections of the stents 12, 14 in order to prevent the stents from becoming embedded in the material of the sheath 114. The bands 121 may be provided in any of a variety of numbers or positions depending upon the stent design. FIG. 10A illustrates the bands positioned at midpoints of each of the four proximal stent sections 127 and each of the five distal stent sections. In an alternative embodiment, the bands 121 are positioned over the ends of adjacent stent sections. The bands 121 may be made of stainless steel, or any other suitable metal or relatively non compliant polymer. Of course, many other structures may also be employed to prevent the self-expanding stents from embedding themselves in the plastic sheath. Such alternative structures may include a flexible coil, a braided tube, a solid-walled tube, or other restraint structures which will be apparent to those skilled in the art in view of the disclosure herein.

The inner surface of the outer sheath 114, and/or the outer surface of the central core 112 may be further provided with a lubricious coating or lining such as Paralene, Teflon, silicone, polyimide-polytetrafluoroethylene composite materials or others known in the art and suitable depending upon the material of the outer sheath 114 and/or central core 112.

As illustrated in FIG. 10B, at least a distal portion of sheath 114 may comprise a two layer construction having an outer tube 210 and an inner tube or coating 212. The exterior surface of the outer tube 210 is preferably adapted to slide easily within the vessels to be treated, while the inner surface is generally adapted to have a low coefficient of static friction with respect to the stents, thus allowing the sheath to slide smoothly over the stents. The outer tube 210 may, for example, be made of or coated with HDPE or PEBAX, and the inner tube 212 may, for example, be made of or coated with HDPE, PTFE, or FEP. In an embodiment in which the inner tube is made with a PTFE liner, however, the distal end 214 of the lubricious inner layer or tube 212 is preferably spaced proximally from the distal end 216 of the outer tube 210 by a distance within the range of from about 1 mm to about 3 mm. This helps prevent the stent from prematurely jumping distally out of the sheath during deployment due to the high lubricity of the PTFE surface.

FIG. 10 illustrates one embodiment of a sheath retraction system. The system illustrated generally includes a sheath pull wire 222, a pull wire slot 224, a sheath retraction band 226, and an outer sheath 114. The sheath retraction band 226 may be a tubular element thermally or adhesively bonded or otherwise secured to a portion of the outer sheath 114. In the illustrated embodiment, the retraction band 226 comprises a section of stainless steel tubing having an outside diameter of about 0.055 inches, a wall thickness of about 0.0015 inches and an axial length of 0.060 inches. However, other dimensions may be readily utilized while still accomplishing the intended function. The sheath retraction band 226 is positioned within the distal portion 117 of the outer sheath 114, just distally of the diameter transition 119. The retraction band 226 may be connected to the interior surface of the outer sheath 114 by heat fusing a pair of bands 225 to the inside surface of the outer sheath at each end of the retraction band (see FIG. 9E). Alternatively, the retraction band 226 can be attached to the outer sheath by using adhesives, epoxies, or by mechanical methods such as crimping and swaging or a combination of these. In this manner, the pull force which would be required to proximally dislodge the retraction band 226 from the outer sheath 114 is greatly in excess of the proximal traction which will be applied to the pull wire 222 in clinical use. The distal end of the pull wire 222 is preferably welded, soldered, bonded, or otherwise secured to the sheath retraction band 226. The pull wire 222 may alternatively be bonded directly to the outer sheath.

The pull wire slot 224 is preferably of sufficient length to allow the sheath 114 to be fully retracted. Thus, the pull wire slot 224 is preferably at least as long as the distance from the distal end of the stent stop 218 to the distal end of the sheath 114 as shown in FIG. 10A. Slot lengths within the range of from about 1 cm to about 10 cm are presently contemplated for a two stent deployment system. With the sheath 114 in the distal position as shown, the pull wire slot 224 is preferably entirely covered by the proximal portion 115 of the sheath 114. Alternatively, in an embodiment in which the proximal extension of sheath 114 extends the entire length of the catheter 100, discussed above, it can be directly attached to the control 150, in which case a pull wire 222 and slot 224 as shown might not be used.

In yet another embodiment illustrated for example in FIGS. 9B and 9C, a pull wire lumen 220 may terminate sufficiently proximally from the retraction band 226 that a slot as shown may not be used.

The pull wire 222 may comprise a variety of suitable profiles known to those skilled in the art, such as round, flat straight, or tapered. The diameter of a straight round pull wire 222 may be between about 0.008" and about 0.018" and in one embodiment is about 0.009". In another embodiment, the pull wire 222 has a multiple tapered profile with diameters of 0.015", 0.012", and 0.009" and a distal flat profile of 0.006"× 0.012". The pull wire 222 may be made from any of a variety of suitable materials known to those skilled in the art, such as stainless steel or nitinol, and may be braided or single strand and may be coated with a variety of suitable materials such as Teflon, Paralene, etc. The wire 222 has sufficient tensile strength to allow the sheath 114 to be retracted proximally relative to the core 112. In some embodiments, the wire 222 may have sufficient column strength to allow the sheath 114 to be advanced distally relative to the core 112 and stents 12, 14. For example, if the distal stent 12 has been partially deployed, and the clinician determines that the stent 12 should be re-positioned, the sheath 114 may be advanced distally relative to the stent 12 thereby re-contracting and capturing that stent on the core.

In general, the tensile strength or compressibility of the pull wire 222 may also be varied depending upon the desired mode of action of the outer sheath 114. For example, as an alternative to the embodiment described above, the outer sheath 114 may be distally advanced by axially distally advancing the pull wire 222, to release the stent 118. In a hybrid embodiment, the outer sheath 114 is split into a proximal portion and a distal portion. A pull wire is connected to the proximal portion, to allow proximal retraction to release the proximal stent. A push wire is attached to the distal portion, to allow distal advance, thereby releasing the distal stent. These construction details of the catheter 100 and nature of the wire 222 may be varied to suit the needs of each of these embodiments, as will be apparent to those skilled in the art in view of the disclosure herein.

The stents 118 are carried on the central support core 112, and are contracted radially thereon. By virtue of this contraction, the stents 118 have a cross section which is smaller than that of the conduits 32 and 34, and they can be introduced into these as will be described below. The stents 118 are preferably disposed on a radially inwardly recessed distal portion 113 of the central core 112 having a smaller diameter than the adjacent portions of the core 112. This recess 113 is preferably adjacent a distal abutment such as a shoulder 124 which may be in the form of a proximally facing surface on a distal tip 122. Distal tip 122 has an outer diameter smaller than that of the stents 118 when the stents are expanded, but greater than the diameter of the stents 118 when they are contracted. This abutment 124 consequently prevents distal advancement of the stents 118 from the core 112 when the stents 118 are contracted.

Proximal movement of the stents 118 relative to the core 112 is prevented when the stents are in the radially contracted configuration by a proximal abutment surface such as annular shoulder 125. The distal abutment 124 and proximal abutment 125 may be in the form of annular end faces formed by the annular recess 113 in the core 112, for receiving the compressed stents 118. See FIG. 12. In one embodiment, illustrated in FIG. 10A, the proximal abutment 125 is carried by a stent stop 218. Stent stop 218 may be integral with or attached to the central core 112, and has an outside diameter such that it is in sliding contact with the inside surface of outer sheath 114. The compressed stent 14 will thus not fit between the stop 218 and the outer sheath 114.

The deployment device 100 typically has a soft tapered tip 122 secured to the distal end of inner core 112, and usually has a guidewire exit port 126 as is known in the art. The tapered distal tip 122 facilitates insertion and atraumatic navigation of the vasculature for positioning the stent system 118 in the area of the bifurcation to be treated. The distal tip 122 can be made from any of a variety of polymeric materials well known in the medical device arts, such as polyethylene, nylon, PTFE, and PEBAX. In the embodiment shown in FIG. 10, the distal tip 122 comprises an annular recess 230 sized and adapted to allow a distal portion of the outer sheath 114 to reside therein such that the transition between the tip and the outer sheath comprises a smooth exterior surface.

The distal tip 122 tapers in one embodiment from an outside diameter which is substantially the same as the outer diameter of the outer sheath 114 at the proximal end 128 of the tip 122 to an outside diameter at its distal end 130 of slightly larger than the outside diameter of a guidewire. The overall length of the distal tip 122 in one embodiment of the delivery catheter 100 is about 3 mm to about 12 mm, and in one embodiment the distal tip is about 8 mm long. The length and rate of taper of the distal tip 122 can be varied depending upon the desired trackability and flexibility characteristics. The tip 122 may taper in a linear, curved or any other manner known to be suitable.

Figure 11B:
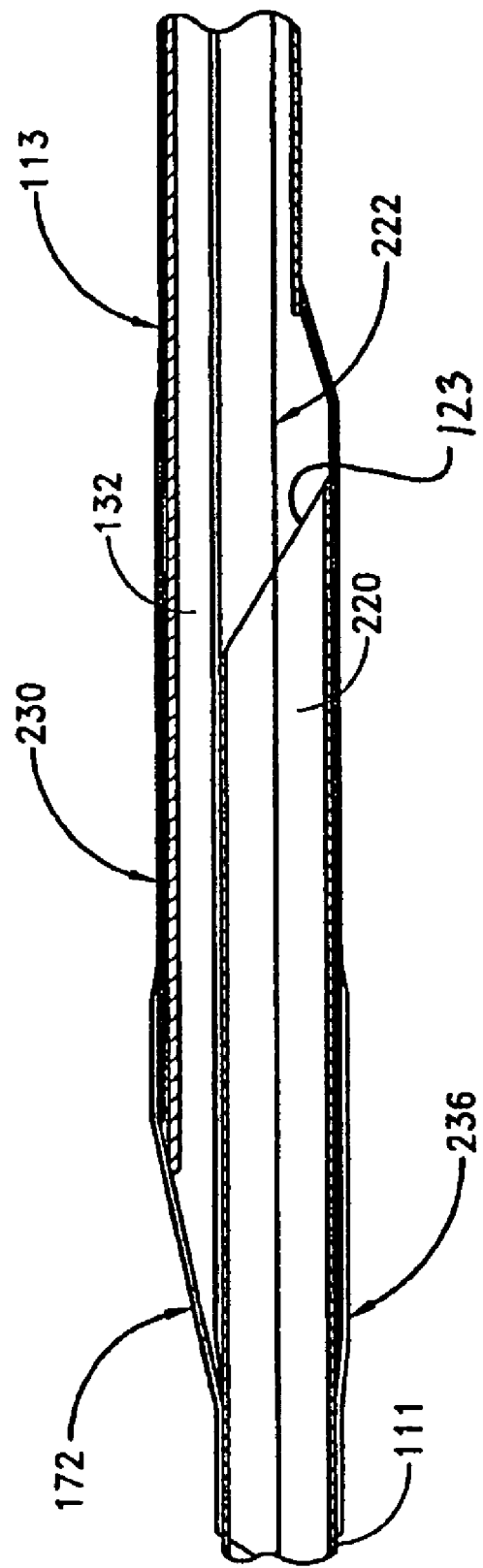
FIG. 11B is a cross sectional view of the transitional portion taken along the line 11B-11B of FIG. 11A.

With reference to FIGS. 11B and 12, a distal portion of the central core 112 preferably has a longitudinal axial lumen 132 permitting slideable engagement of the core 112 on a guidewire 170. The guidewire lumen 132 preferably includes a proximal access port 172 and a distal access port 126 through which the guidewire may extend. The proximal access port 172 may be located at a point along the length of the catheter 100, as shown in FIGS. 11A and 11B, and discussed below (rapid exchange), or the proximal access port 172 may be located at the proximal end 102 of the catheter 100 (over the wire). In a rapid exchange embodiment, the proximal access port 172 is generally within about 25 cm of the distal access port 126, and preferably is between about 20 cm and about 30 cm of the distal access port 126. The guidewire lumen 132 may be non-concentric with the catheter centerline for a substantial portion of the length of the guidewire lumen 132.

FIGS. 11A and 11B illustrate a transition between a proximal shaft tube 111 and a distal shaft tube 113 including a proximal guidewire access port 172 and a guidewire lumen 132. The guidewire lumen 132 may extend through a coextrusion, or may be a separate section of tubing which may be bonded, bound by a shrink wrap tubing, or otherwise held relative to the proximal shaft tube 111.

In the construction shown in cross-section in FIG. 11B, a proximal shaft tube 111 having a pull wire lumen 220 is joined to a distal shaft tube 113 having a continuation of pull wire lumen 220 as well as a guidewire lumen 132. In the illustrated embodiment, the proximal shaft tube 111 extends distally into the proximal end of connector tubing 230. A mandrel is positioned within each lumen, and shrink tubing 236 is heated to bond the joint. An opening is subsequently formed in the shrink wrap to produce proximal access port 172 which provides access to the guidewire lumen 132.

In one embodiment, the proximal shaft tube 111 comprises a stainless steel hypodermic needle tubing having an outside diameter of about 0.025" and a wall thickness of about 0.003". The distal end 123 of the hypotube is cut or ground into a tapered configuration. The axial length of the tapered zone may be varied widely, depending upon the desired flexibility characteristics of the catheter 100. In general, the axial length of the taper is within the range of from about 1 cm to about 5 cm, and, in one embodiment, is about 2.5 cm. Tapering the distal end of the hypotube at the transition with the distal portion of the catheter provides a smooth transition of the flexibility characteristics along the length of the catheter, from a relatively less flexible proximal section to a relatively more flexible distal section as will be understood by those of skill in the art.

Referring to FIG. 12, a guidewire 170 is illustrated as positioned within the guidewire lumen 132. As can be appreciated by those of skill in the art, the diameter of the guidewire 170 is illustrated as slightly smaller (e.g., by about 0.001-0.003 inches) than the inside diameter of the guidewire lumen 132. Avoiding a tight fit between the guidewire 170 and inside diameter of guidewire lumen 132 enhances the slideability of the catheter over the guidewire 170. In ultra small diameter catheter designs, it may be desirable to coat the outside surface of the guidewire 170 and/or the inside walls of the guidewire lumen 132 with a lubricous coating to minimize friction as the catheter 100 is axially moved with respect to the guidewire 170. A variety of coatings may be utilized, such as Paralene, Teflon, silicone, polyimide-polytetrafluoroethylene composite materials or others known in the art and suitable depending upon the material of the guidewire 170 or central core 112.

As shown in FIG. 12, an inflation lumen 134 may also extend throughout the length of the catheter 100 to place a proximal inflation port in fluid communication with one or more inflatable balloons 116 carried by the distal end of the catheter.

The inflatable balloon 116, if present, may be positioned beneath one or both stents, such as stent 14 as illustrated in FIG. 12 or proximally or distally of the stent, depending upon the desired clinical protocol. In one embodiment, as illustrated in FIG. 12, the stent may be a self expandable stent which is initially released by proximal retraction by the outer sheath 114 as has been discussed. The balloon 16 is thereafter positioned in concentrically within the stent, such that it may be inflated without repositioning the catheter to enlarge and/or shape the stent. Post stent deployment dilatation may be desirable either to properly size and or shape the stent, or to compress material trapped behind the stent to increase the luminal diameter (e.g. angioplasty). In an alternate mode of practicing the invention, angioplasty is accomplished prior to deployment of the stent either by a balloon on the stent deployment catheter 100 or by a separate angioplasty balloon catheter (or rotational artherectomy, laser or other recanalization device). The stent deployment catheter 100 is thereafter positioned within the dilated lesion, and the stent is thereafter deployed. Thus, balloon dilatation can be accomplished using either the deployment catheter 100 or separate procedural catheter, and may be accomplished either prior to, simultaneously with, or following deployment of one or more stents at the treatment site.

As seen in FIGS. 9 and 9B, the catheter also includes a handpiece 140 at the proximal end of the catheter 100. The handpiece 140 is adapted to be engaged by the clinician to navigate and deploy the stent system 118 as will be described below. The handpiece 140 preferably includes a control 150 adapted to control and indicate a degree of deployment of one or both stents. The control 150 is typically in mechanical communication with the sheath 114 such that proximal retraction of the control 150 results in proximal retraction of the sheath 114. Those skilled in the art will recognize that distal motion, rotational movement of a rotatable wheel, or other motion of various controls 150 may alternatively be employed to axially move such as distally advance or proximally retract the sheath 114 to expose the stents.

The illustrated control 150 is preferably moveable from a first position to a second position for partial deployment of the first stent 12, and a third position for complete deployment of the first stent 12. A fourth and a fifth positions are also provided to accomplish partial and complete deployment of the second stent 14. The control 150 may include indicia 160 adapted to indicate the amount of each stent 12 or 14 which has been exposed as the sheath 114 is retracted relative to the core 112. The indicia 160 may include dents, notches, or other markings to visually indicate the deployment progress. The control 150 may also or alternatively provide audible and/or tactile feedback using any of a variety of notches or other temporary catches to cause the slider to "click" into positions corresponding to partial and full deployment of the stents 12, 14. Alignable points of electrical contact may also be used. Those skilled in the art will recognize that many methods and structures are available for providing a control 150 as desired.

The catheter 100 may include a plurality of radiopaque markers 250 (seen best in FIGS. 2, 10, and 10A) impressed on or otherwise bonded to it, containing a radiopaque compound as will be recognized by those skilled in the art. Suitable markers can be produced from a variety of materials, including platinum, gold, barium compounds, and tungsten/rhenium alloy. Some of the markers 250A may have an annular shape and may extend around the entire periphery of the sheath 114. The annular markers 250A may be situated, in the area of the distal end of the first stent 12, the distal end of the second stent 14, and in the area of the bridge 18 (FIG. 1) or space separating the stents 12, 14. A fourth marker 252 may be situated at substantially the halfway point of the generatrix of the lower segment of the second stent 14 situated in the continuation of the bridge 18 and of the diametrically opposite generatrix. FIG. 2 shows a marker 252 with a diamond shape and a small thickness provided along the outer sheath 114 at a desirable position for determining the rotational position of the catheter within the bifurcation. The markers 250, 252, 254 may be impressed on the core 112, on the sheath 114, or directly on the stents 12, 14 such as on the bridge 18, and not on the sheath 114.

With reference to FIGS. 10 and 10A, three markers 253 are shown disposed at a distal end of the second stent 14 and spaced at 120° relative to one another. Three markers 254 are also disposed at a proximal end of the first stent 12, and spaced at 120° relative to one another. Each stent 12, 14 also includes a single marker 250, 210 at its opposite end (e.g. the first stent 12 has a single marker 250 at its distal end, and the second stent 14 has a single marker 210 at its proximal end). Of course, other marker arrangements may be used as desired by the skilled artisan.

A central marker 252 makes it possible to visualize, with the aid of a suitable radiography apparatus, the position of a bridge 18 separating the two stents 12, 14. Thus allowing a specialist to visualize the location of the second stent 14 so that it can be correctly positioned in relation to the widened zone 46. The end markers 250A allow a specialist to ensure that the stents 12, 14 are correctly positioned, respectively, in the main/principal conduit 32 and the secondary/branch conduit 34.

A diamond-shaped marker 252 as shown in FIG. 2 is, for its part, visible in a plan view or an edge view, depending on whether it is oriented perpendicular or parallel to the radius of the radiography apparatus. It thus makes it possible to identify the angular orientation of the stents 12, 14 in relation to the bifurcation 30, so that the part of the second stent 14 having the greatest expansion can be placed in an appropriate manner in relation to the widened transition zone 46.

Methods of positioning and deploying a pair of dissimilar stents in an area of a bifurcation will now be discussed with reference to FIGS. 3-6 and 13-17. Although portions of the following discussion refer to delivery of two dissimilar stent portions, those skilled in the art will recognize that a larger or smaller number of stents, and/or stents having similar expanded configurations may also be used while realizing certain aspects of the present invention.

A method of delivering a stent system as described above generally and illustrated in FIGS. 13-17 includes locating the bifurcation 30 to be treated, providing a suitable delivery catheter 100, positioning the distal portion 107 of a delivery catheter with stents 12, 14 disposed thereon in the branch of the bifurcation to be treated, partially deploying the first stent 12 in a branch vessel 34, observing and adjusting the position of the first stent 12 if necessary, then fully deploying the first stent 12. The second stent 14 is partially deployed, and preferably the position is again observed such as by infusing contrast media through the pull wire lumen 220 under fluoroscopic visualization. The position of the second stent 14 may be adjusted if necessary, and finally the second stent 14 is fully deployed. Methods of navigating catheters through blood vessels or other fluid conduits within the human body are well known to those skilled in the art, and will therefore not be discussed herein.

The delivery catheter 100 may be constructed according to any of the embodiments described above such that the stents 12, 14 may be selectively deployed by axially displacing the outer sheath 114 along the delivery catheter, thereby selectively exposing the stent system 10. This may be accomplished by holding the sheath 114 fixed relative to the bifurcation, and selectively distally advancing the central core 112. Thus, the present invention contemplates deploying one or more stents by distally advancing the central core (inner sheath) rather than proximally retracting the outer sheath as a mode of stent deployment. The stent system may alternatively be deployed by holding the central core fixed relative to the bifurcation and selectively proximally retracting the sheath 114. The catheter may also be adapted to allow the sheath to be advanced distally, thereby re-contracting the partially deployed stents on the central core 112 to allow repositioning or removal.

In order to visualize the position of a partially-deployed stent with a suitable radiographic apparatus, a contrast media may be introduced through the catheter to the region of the stent placement. Many suitable contrast media are known to those skilled in the art. The contrast media may be introduced at any stage of the deployment of the stent system 10. For example, a contrast media may be introduced after partially deploying the first stent 12, after fully deploying the first stent 12, after partially deploying the second stent 14, or after fully deploying the second stent 14.

The degree of deployment of the stent system 10 is preferably made apparent by the indicators on the handpiece 200 as described above. The handpiece 200 and outer sheath are preferably adapted such that a motion of a control on the handpiece 200 results in proximal motion of the outer sheath 114 relative to the distal tip 122 and the stents 12, 14. The handpiece 140 and sheath 114 may also be adapted such that the sheath may be advanced distally relative to the stents 12, 14, thus possibly re-contracting one of the stents 12, 14 on the core 112. This may be accomplished by providing a pull wire 222 having a distal end 223 attached to a portion of the outer sheath 114, and a proximal end adapted to be attached to the handpiece 200. Alternatively, the handpiece 200 may be omitted, and the retraction wire 206 may be directly operated by the clinician.

Figure 4:
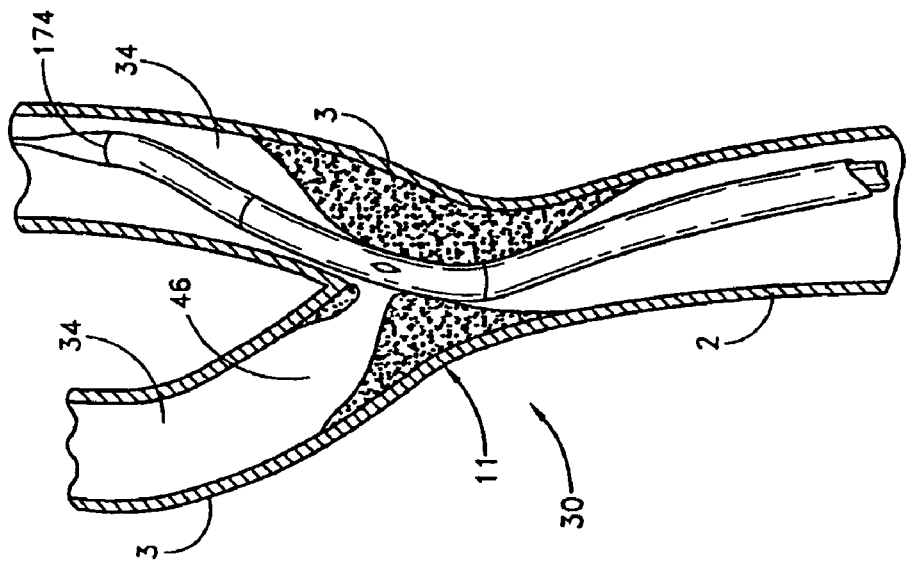
FIG. 4 is a section view of the bifurcation of FIG. 3 showing a delivery catheter positioned therein.
Figure 6:
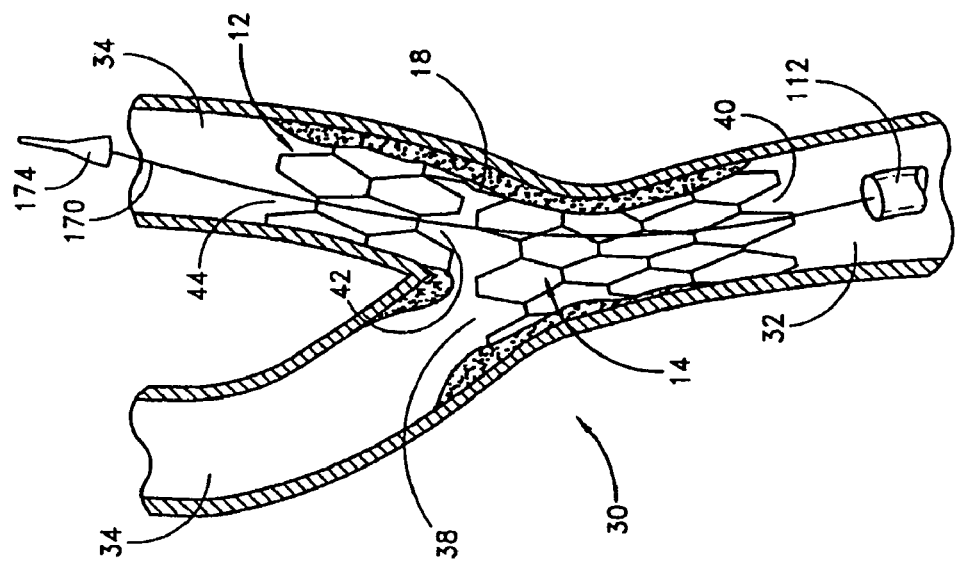
FIG. 6 is a section view of the bifurcation of FIG. 3 showing an embodiment of a stent system shown in an expanded and fully deployed state.
Figure 5:
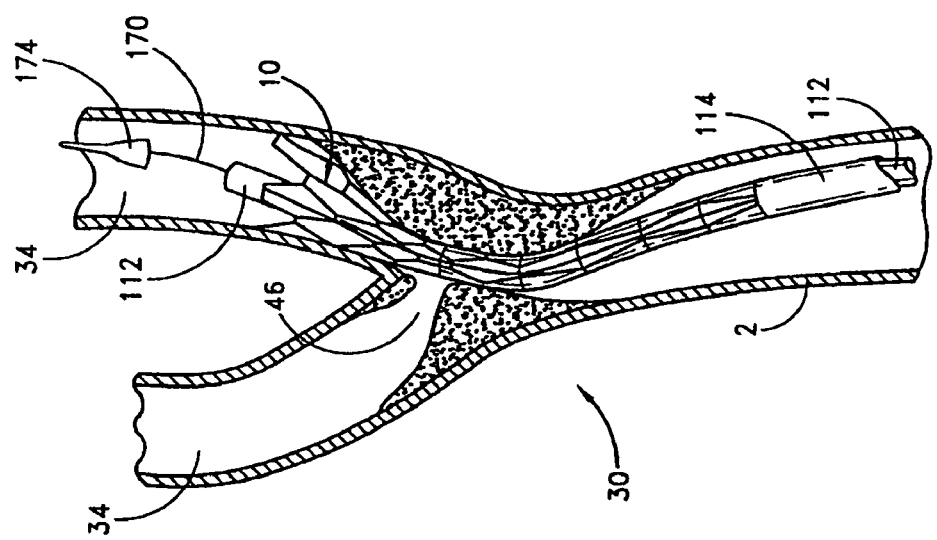
FIG. 5 is a section view of the bifurcation of FIG. 3 showing an embodiment of a stent system shown in a partially contracted state on a portion of a delivery catheter.

In an alternative embodiment, indicated by FIGS. 4-6, the first and/or second stent 12, 14 may be deployed in a single motion, thus omitting the step of re-positioning the stent 12, 14 before fully deploying it. The sheath 114 is then progressively withdrawn, as is shown in FIGS. 5 and 6, in order to permit the complete expansion of the stents 12, 14.

In a preferred embodiment, the second stent 14 is placed in close proximity to the first stent 12. For example, the distal end 38 of the second stent 14 may be placed within a distance of about 4 mm of the proximal end 42 of the first stent 12, more preferably this distance is less than about 2 mm, and most preferably the first and second stents 12, 14 are placed within 1 mm of one another. Those skilled in the art will recognize that the relative positioning of the first and second stents 12, 14 will at least partially depend on the presence or absence of a bridge 18 as discussed above. The axial flexibility of any bridge 18 will also affect the degree of mobility of one of the stents relative to the other. Thus, a stent system 10 will preferably be chosen to best suit the particular bifurcation to be treated.

As mentioned above, the stents 12, 14 may be self-expanding or balloon-expandable (e.g. made of a substantially non-elastic material). Thus the steps of partially deploying the first and/or the second stent may include introducing an inflation fluid into a balloon on which a stent is disposed, or alternatively the stent may be allowed to self-expand. In the case of a balloon-expandable second stent 14, the balloon 116 (FIG. 12A) on which the second stent 14 is disposed may be specifically adapted to correspond to the particular shape of the second stent 14. Specifically, such a balloon will preferably have a larger diameter at a distal end than at a proximal end.

Figure 17:
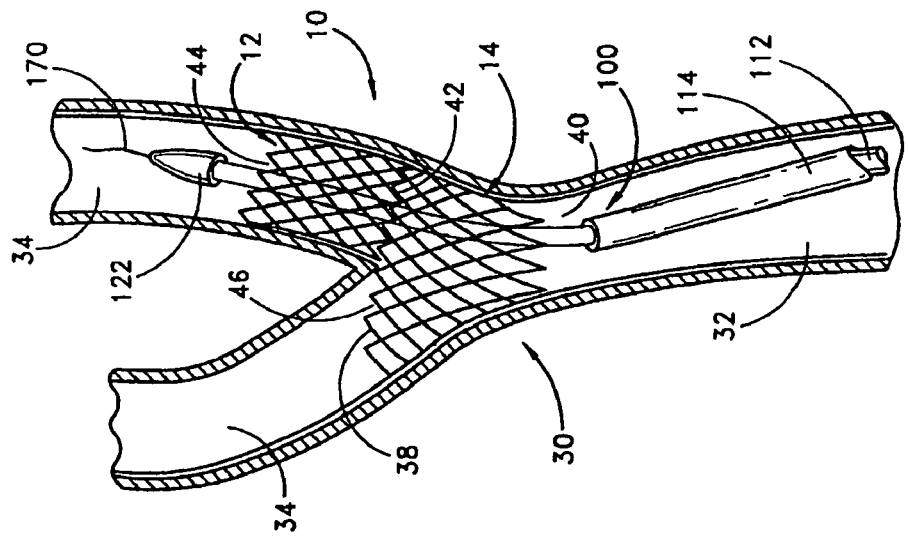
FIG. 17 is a section view of a bifurcation showing a second stent in a fully deployed state.
Figure 16:
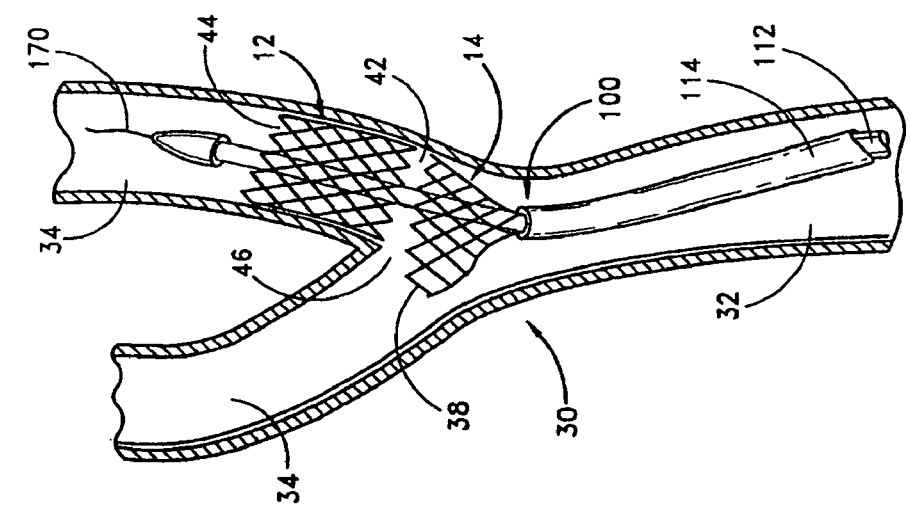
FIG. 16 is a section view of a bifurcation showing a second stent in a partially deployed state.
Figure 15:
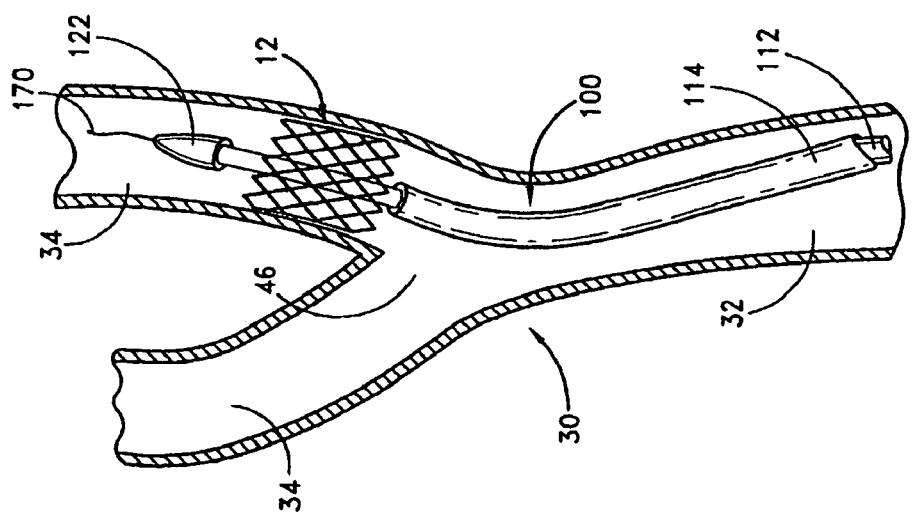
FIG. 15 is a section view of a bifurcation showing a first stent in a fully deployed state.

After complete expansion of the stents 12, 14, the distal end of the delivery catheter 100 including the core 112 and the guidewire 170 may be withdrawn from the conduits and the vasculature of the patient. Alternatively, additional stents may also be provided on a delivery catheter, which may also be positioned and deployed in one or both branches of the bifurcation. For example, after deploying the second stent 14 as shown in FIG. 6 or 17, the catheter 100 and guidewire 170 may be retracted and re-positioned in the second branch vessel such that a third stent may be positioned and deployed therein.

Figure 18:
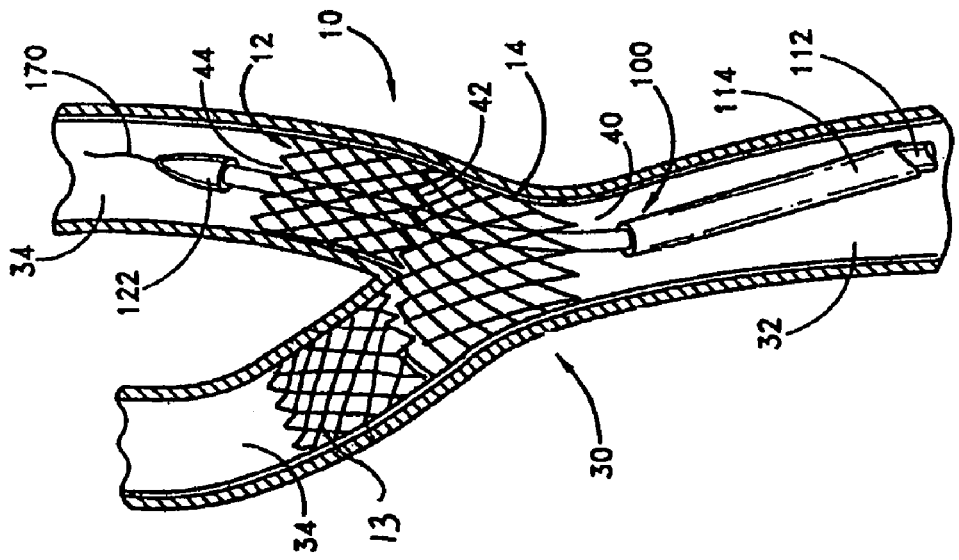
FIG. 18 is a section view of a bifurcation as in FIG. 17, with a second branch stent deployed in the second branch.

Referring to FIG. 18, a second branch stent 13 may be deployed in the second branch, such that both branch vessels in the bifurcation are fully stented. The second branch stent 13 may be either a self expandable or balloon expandable stent such as those well known in the art and disclosed in part elsewhere herein. The second branch stent 13 may be deployed before or after the main stent 14 and/or first branch stent 12. In one application of the invention, the main vessel stent 14 and first branch stent 12 are positioned as has been described herein. A stent deployment catheter (not illustrated) such as a balloon catheter or self expanding stent deployment catheter is transluminally advanced to the bifurcation, and advanced through the main vessel stent 14. The second branch vessel stent 13 may then be aligned in the second branch vessel, such that it abuts end to end, is spaced apart from, or overlaps with the distal end of the main branch stent 14. The second branch vessel stent 13 may then be deployed, and the deployment catheter removed.

As will be clear to those skilled in the art, the stent system 10 and stent delivery system 100 described herein is useful in treating a number of pathological conditions commonly found in vascular systems and other fluid conduit systems of human patients. Treatment with the apparatus can include re-establishing the appropriate diameter of a bifurcation in cases of arteriosclerosis or internal cell proliferation, or in rectifying a localized or nonlocalized dissection in the wall of the conduit, or in re-creating a bifurcation of normal diameter while eliminating the aneurysmal pouch in cases of aneurysm.

One or more of the stents deployed in accordance with the present invention may be coated with or otherwise carry a drug to be eluted over time at the bifurcation site. Any of a variety of therapeutically useful agents may be used, including but not limited to, for example, agents for inhibiting restenosis, inhibiting platelet aggregation, or encouraging endothelialization. Some of the suitable agents may include smooth muscle cell proliferation inhibitors such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine; antimicrobials such astriclosan, cephalosporins, aminoglycosides, and nitorfuirantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promotors; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Intergrilin, abciximab), seratonin antagonist, and 5-HT uptake inhibitors; cholesterol-lowering agents; vasodilating agents; and agents which interfere with endogeneus vascoactive mechanisms. Polynucleotide sequences may also function as anti-restenosis agents, such as p15, p16, p18, p19, p21, p27, p53, p57, Rb, nFkB and E2F decoys, thymidine kinase ("TK") and combinations thereof and other agents useful for interfering with cell proliferation. The selection of an active agent can be made taking into account the desired clinical result and the nature of a particular patient's condition and contraindications.

The bifurcation 30 shown in FIG. 3 has excrescences 35 which create a narrowing in cross section, which impedes the flow of the liquid circulating in the conduits 32 and 34. In the case of a vascular bifurcation, these excrescences are due, for example, to arteriosclerosis or cellular growth. The stent system described herein permits treatment of this bifurcation by re-establishing the appropriate diameter of the conduits 32, 34 and of the widened transition zone 46.

Figure 7:
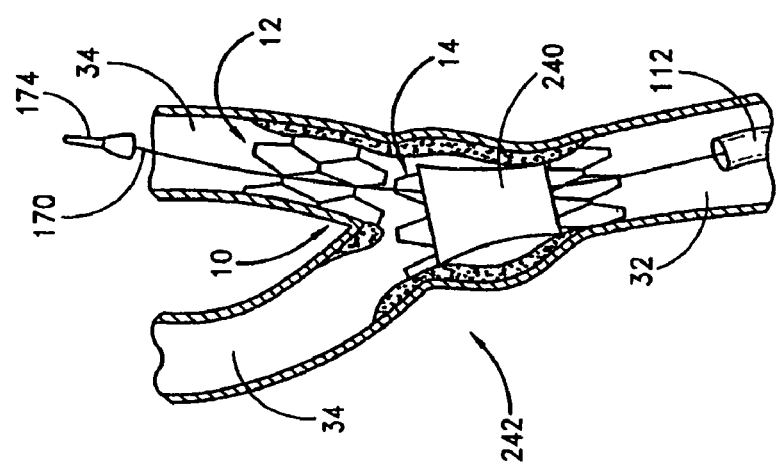
FIG. 7 is a section view of a bifurcation presenting an aneurysm and an embodiment of a stent system shown deployed therein.

As shown in FIG. 7, the stent system 10 can also be used to treat an aneurysm 242. An aneurysm 242 is defined as a localized, pathological, blood-filled dilatation of a blood vessel caused by a disease or weakening of the vessel's wall. Thus it is desirable to provide a "substitute" vessel wall in an area of an aneurysm. For this purpose, the first or second stent 12, 14 may be at least partially covered by a film 240 which is substantially impermeable to the liquid circulating in the conduits 32, 34. Many suitable films are known to those skilled in the art such as polyester, polytetrafluoroethylene (PTFE), high and medium density polyethylenes, etc. The film may be sewn onto the stents 12, 14, or it may be folded around a stent such that as the stent is expanded within the vessel 32, the film 240 is trapped and held between the stent and the vessel wall. The stent then guides the liquid through the bifurcation 30 and consequently prevents stressing of the wall forming the aneurysm 242.

The stent system described may be adapted as mentioned above to treat any of a number of bifurcations within a human patient. For example, bifurcations of both the left and right coronary arteries, the bifurcation of the circumflex artery, the carotid, femoral, iliac, popliteal, renal or coronary bifurcations. Alternatively this apparatus may be used for nonvascular bifurcations, such as tracheal or biliary bifurcations, for example between the common bile and cystic ducts, or in the area of the bifurcation of the principal bile tract.

Although certain preferred embodiments and examples have been described herein, it will be understood by those skilled in the art that the present inventive subject matter extends beyond the specifically disclosed embodiments to other alternative embodiments and/or uses of the invention and obvious modifications and equivalents thereof. Thus, it is intended that the scope of the present inventive subject matter herein disclosed should not be limited by the particular disclosed embodiments described above, but should be determined only by a fair reading of the claims that follow.

What is claimed is:

1. A deployment system for treating a bifurcation of a main vessel and first and second branch vessels, comprising:
    an elongate, flexible body, having a proximal end and a distal end;
    a single stent carried by the distal end of the body, the single stent comprising a proximal, upstream end, and a distal, downstream end, and a stent wall extending therebetween;
    a releasable restraint, for retaining the stent on the flexible body, the releasable restraint comprising an axially moveable outer sheath having a lubricious layer, wherein a distal end of the lubricious layer is spaced proximally from the outer sheath's distal end, thereby providing a section of the releasable restraint at the outer sheath's distal end region that is free of the lubricious layer; and
    a distal tip comprising an annular recess formed therein configured to receive the releasable restraint's distal end, wherein the annular recess at least partially overlaps the lubricious layer;
    wherein the distal, downstream end of the stent is larger in diameter than the proximal, upstream end of the stent in an unconstrained expanded configuration, and wherein the stent wall defines a single central lumen and is radially symmetrically disposed about the longitudinal axis of the flexible body when retained on the body.

2. A deployment system as in claim 1, further comprising a guidewire lumen extending axially through at least a portion of the flexible body.

3. A deployment system as in claim 2, wherein the guidewire lumen has a proximal access port and a distal access port, and the proximal access port is positioned along the flexible body, spaced distally apart from the proximal end.

4. A deployment system as in claim 2, wherein the guidewire lumen has a proximal access port and a distal access port, and the proximal access port is positioned at the proximal end of the flexible body.

5. A deployment system as in claim 1, wherein the releasable restraint comprises an axially movable control element extending along a length of the flexible body.

6. A deployment system as in claim 1, wherein the releasable restraint further comprises a pull wire.

7. A deployment system as in claim 1, wherein the releasable restraint further comprises a dissolvable media.

8. A deployment system as in claim 1, wherein the expanded diameter of the single stent tapers radially outwardly in the distal direction.

9. A deployment system as in claim 1, wherein the stent wall is configured to contact and support a wall of the bifurcation from the proximal, upstream end to the distal, downstream end when the stent is deployed in the bifurcation.

10. A deployment system as in claim 1, wherein the stent is uncovered.

11. A deployment system as in claim 1, wherein the lubricious layer is spaced a distance within the range of from about 1 mm to about 3 mm from the outer sheath's distal end.

12. A deployment system as in claim 1, wherein the releasable restraint comprises a plurality of expansion limiting bands.

13. A deployment system as in claim 1, wherein the stent comprises a drug capable of being eluted over time.

14. A stent deployment catheter, comprising:
    an elongate, flexible tubular body, having a proximal end and a distal end;
    a noncylindrical, self-expandable stent carried by the distal end, the stent comprising a proximal end, a distal end, and a stent wall extending therebetween, the stent distal end having a larger diameter than the stent proximal end in an unconstrained expanded configuration, wherein the stent is positioned on the distal end of the tubular body such that the stent distal end is located distally relative to the stent proximal end;
    a releasable restraint comprising an axially moveable sheath, covering the noncylindrical, self-expandable stent, wherein a distal portion of the sheath comprises a lubricious layer spaced proximally from a distal end of the sheath;
    a distal tip comprising an annular recess formed therein configured to receive the distal end of the sheath, wherein the annular recess at least partially overlaps the lubricious layer; and
    a handpiece on the proximal end, wherein the handpiece comprises a control and first and second indicia that indicate partial and complete uncovering of the stent with the sheath when the control is aligned with said first and second indicia, respectively, and wherein the control is configured to be moved from an initial position in which the stent is covered to said first and second indicia.

15. A stent deployment catheter as in claim 14, further comprising a guidewire lumen, in an over the wire configuration.

16. A stent deployment catheter as in claim 14, further comprising a guidewire lumen, in a rapid exchange configuration.

17. A stent deployment catheter as in claim 14, wherein the indicia comprises a marking on the handpiece.

18. A stent deployment catheter as in claim 14, wherein the indicia provides tactile feedback to indicate when said control is aligned with said indicia.

19. A deployment system as in claim 14, wherein the stent comprises a drug capable of being eluted over time.

* * * * *